US005981248A

United States Patent [19]

Xu

[11] Patent Number: 5,981,248
[45] Date of Patent: Nov. 9, 1999

[54] MAMMALIAN CELL DEATH PREVENTING KINASE, DPK

[75] Inventor: Hua Xu, Thousand Oaks, Calif.

[73] Assignee: Amgen Inc., Thousand Oaks, Calif.

[21] Appl. No.: 08/969,630

[22] Filed: Nov. 13, 1997

[51] Int. Cl.$^6$ ........................................................ C12N 9/12
[52] U.S. Cl. ............................................ 435/194; 435/193
[58] Field of Search ................................... 435/194, 193; 530/300, 350, 358

[56] References Cited

FOREIGN PATENT DOCUMENTS

97/09432  3/1997  WIPO .

OTHER PUBLICATIONS

Hoang et al, "Participation of cyclin A in Myc–induced apoptosis," PNAS USA, vol. 91, No. 15, pp. 6875–6879 (1994).

Schultz et al. Identification of 21 novel human protein kinases, including 3 members of a family related to the cell cycle regulator nimA of Aspergillus nidulans. Cell Growth and Differentiation. 4: 821–830, Oct., 1993.

The Merck Index, eighth edition. NJ: Merck & Co, Inc. p. 497, 1968.

Broome, et al., "Apoptosis and Bcl–2 expression in cultured murine splenic T cells," Immunology, vol. 84, pp. 375–382, 1995.

Broome, et al., "Expression of Bcl–2, Bcl–x, and Bax after T Cell Activation and IL–2 Withdrawal," The Journal of Immunology, vol. 155:2311–2317, 1995.

Collins et al., "The cell cycle and cancer," Proc.Natl.Acad.Sci.USA, vol. 94, pp. 2776–2778, Apr. 1997.

Deng, et al., "Suppression of apoptosis in a cytotoxic T–cell line by interleukin 2–mediated gene transcription and deregulated expression of the protooncogene bcl–2," Proc.Natl.Acad.Sci.USA, vol. 90, pp. 2189–2193, Mar. 1993.

Edgar et al., "Distinct molecular mechanisms regulate cell cycle timing at successive stages of Drosophila embryogenesis," Genes & Development, vol. 8:440–452, 1994.

Elledge, "Cell Cycle Checkpoints: Preventing an Identity Crisis," Science, vol. 274, pp. 1664, Dec. 1996.

Fang et al., "Cloning and Molecular Characterization of Mouse bcl–x in B and T Lymphocytes," The Journal of Immunology, vol. 153:4388, 1994.

Gonzalez–Garcia et al., "bcl–$x_L$ is the major bcl–x mRNA form expressed during murine development and its product localizes to mitochondria," Development, vol. 120, pp. 3033–3042, 1994.

Hanks et al., "The Protein Kinase Family: Conserved Features and Deduced Phylogeny of the Catalytic Domains," Science, vol. 241, pp. 42, 1988.

Hunter et al., "Cyclins and Cancer II: Cyclin D and CDK Inhibitors Come of Age," Cell, vol. 79, pp. 573–582, Nov. 1994.

Leclerc et al., "Drosophila Cdk8, a Kinase Partner of Cyclin C that Interacts with the Large Subunit of RNA Polymerase II," Molecular Biology of the Cell, vol. 7, pp. 505–513, Apr. 1996.

Matsushime et al., "Identification and Properties of an Atypical Catalytic Subunit (p34$^{PSK–J3}$/cdk4) for Mammalian D Type G1 Cyclins," Cell, vol. 71, pp. 323–334, Oct. 1992.

Morgan, "Principles of CDK regulation," Nature, vol. 374, pp. 131, Mar. 1995.

Nasmyth, "Viewpoint: Putting the Cell Cycle in Order," Science, vol. 274, pp. 1643, Dec. 1996.

Negrini et al., "Molecular Analysis of mbcl–2: Structure and Expression of the Murine Gene Homologous to the Human Gene Involved in Follicular Lymphoma," Cell, vol. 49, pp. 455–463, May 1987.

Nourse et al., "Interleukin–2–mediated elimination of the p27$^{Kip1}$ cyclin–dependent kinase inhibitor prevented by rapamycin," Nature, vol. 372, pp. 570–573, Dec. 1994.

Nunez, et al., "Deregulated Bcl–2 Gene Expression Selectively Prolongs Survival of Growth Factor–Deprived Hemopoietic Cell Lines," The Journal of Immunology, vol. 144, pp. 3602–3610, May 1, 1990.

Oltvai et al., "Bcl–2 Heterodimerizes In Vivo with a Conserved Homolog, Bax, That Accelerates Programmed Cell Death," Cell, vol. 74, pp. 609–619, Aug. 1993.

Reed, "Double identity for proteins of the Bcl–2 family," Nature, vol. 387, pp. 773–776, Jun. 1997.

Reed, "Regulation of apoptosis by bcl–2 family proteins and its role in cancer and chemoresistance," Current Opinion in Oncology, vol. 7:541–546, 1995.

Rudin et al., "Apoptosis and Disease: Regulation and Clinical Relevance of Programmed Cell Death," Annu.Rev.Med. 48:267–81, 1997.

Salomini et al., "Resistance to apoptosis in CTLL–2 cells constitutively expressing c–Myb is associated with induction of BCL–2 expression and Myb–dependent regulation of bcl–2 promoter activity," Proc.Natl.Acad.Sci.USA, vol. 94, pp. 3296–3301, Apr. 1997.

Sherr, "Cancer Cell Cycles," Science, vol. 274, pp. 1672, Dec. 1996.

Siliciano et al., "itk, a T–cell–specific tyrosine kinase gene inducible by interleukin 2," Proc.Natl.Acad.Sci.USA, vol. 89, pp. 11194–11198, 1992.

Stillman, "Cell Cycle Control of DNA Replication," Science, vol. 274, pp. 1659, Dec. 1996.

(List continued on next page.)

Primary Examiner—Bradley L. Sisson
Assistant Examiner—Gabriele E. Bugaisky
Attorney, Agent, or Firm—S. Odre; R. Cook

[57] ABSTRACT

Disclosed are nucleic acids encoding novel proteins, designated DPK. Also disclosed are amino acid sequences for DPK polypeptides, methods for preparing DPK polypeptides, and other related aspects.

4 Claims, 20 Drawing Sheets

OTHER PUBLICATIONS

Surosky et al., "The Yeast UME5 Gene Regulates the Stability of Meiotic mRNAs in Response to Glucose," Molecular and Cellular Biology, vol. 14, pp. 3446–3458, May 1994.

Tassan et al., Identification of human cyclin–dependent kinase 8, a putative protein kinase partner for cyclin C, Proc.Natl.Acad.Sci.USA, vol. 92, pp. 8871–8875, Sep. 1995.

Weller, et al., "Transforming growth factor–$\beta_2$ induces apoptosis of murine T cell clones without down–regulating bcl–2 mRNA expression," Eur.J.Immunol., vol. 24:1293–1300, 1994.

Yang, et al., "Bad, a Heterodimeric Partner for Bcl–$x_L$ and Bcl–2, Displaces Bax and Promotes Cell Death," Cell, vol. 80, pp. 285–291, Jan. 1995.

FIG. 1A
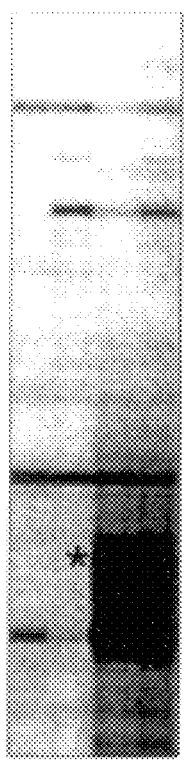
+ + − −
1 2 3 4
FIG. 1B
+ −
1 2
DPK
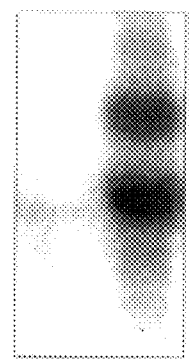
β-Actin
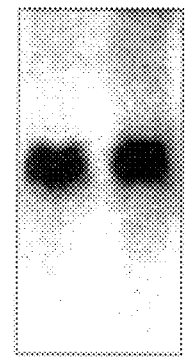

FIG. 2A-1 human DPK

```
     TGTGCCGCCGAGGAGTCCCTTGCTGAAGGCGGACCGCGAGCGGCGGCGGCGGCGGCGAGAGGCGGCTGTTGG
     AGAAGTGGAGCGGCGGTCGCGGGGGGAGGAGGAGGACTGAGCGGTCGCGGCCCCGTGCCTCTATGGGAAGCAGACA
  1  M  D  Y  D  F  K  A  K  L  A  A  E  R  E  R  V  E  D  L  F  E  Y  E  G  C  K  V  G  R  G
     ATGGATTATGATTTCAAGGCGAAGCTGGCGGCGGAGCGGGTGGAGGATTTGTTTGAGTACGAAGGTGCAAAGTGGACGCGGC
 31  T  Y  G  H  V  Y  K  A  R  R  K  D  G  K  D  E  K  E  Y  A  L  K  Q  I  E  G  T  G  I  S
     ACCTACGGTCACGTCTACAAGGCGAGGCGGAAAGATGGGAAAGATGAAAAAGAATATGCATTGAAGCACAGGAATATCC
 61  M  S  A  C  R  E  I  A  L  L  R  E  L  K  H  P  N  V  I  A  L  Q  K  V  F  L  S  H  S  D
     ATGTCGGCTTGTAGAGAGATTGCACTTTTGCGAGAATTGAAGCACCCTAATGTGATTGCAGAAGGTGTTCCTTTCTCACAGTGAC
 91  R  K  V  W  L  F  D  Y  A  E  H  D  L  W  H  I  I  K  F  H  R  A  S  K  A  N  K  K  P
     AGGAAGGTATGGCTGTTTGATTATGCAGAGCATGATCTGTGGCATATTATTAAGTTTCACCGTGCATCAAAAGCAAATAAAAAGCCC
121  M  Q  L  P  R  S  M  V  K  S  L  L  Y  Q  I  L  D  G  I  H  Y  L  H  A  N  W  V  L  H  R
     ATGCAGTTGCCAAGATCTATGGTTAAAATCCTACTTTACCAGATTCTTGATGGTATCCATTACCTCCATGCAAATTGGGTGCTTCACAGA
151  D  L  K  P  A  N  I  L  V  M  G  E  P  E  R  G  R  V  K  I  A  D  M  G  F  A  R  L  F
     GACTTGAAACCTGCAAATATCCTAGTAATGGGAGAAGTCCTGAGAGGGGAGAGTCAAAATAGCTGACATGGGTTTTGCCAGATTATTC
181  N  S  P  L  K  P  L  A  D  L  D  P  V  V  V  T  F  W  Y  R  A  P  E  L  L  L  G  A  R  H
     AATTCCTCCTAAAGCCACTAGACAGATTTGGATCCAGTAGTTGTGACATTTTGGTATCGGGCTCCAGAACTTTTGCTTGTTGGTGCAAGGCAT
211  Y  T  K  A  I  D  I  W  A  I  G  C  I  F  A  E  L  L  T  S  E  P  I  F  H  C  R  Q  E  D
     TATACAAAAGCCATTGATATATGGGCAATAGGTTGTATATTTGCTGAATTGTTGACTTCGGAACCTATTTTTCACTGTCGTCAGGAAGAT
241  I  K  T  S  N  P  F  H  H  D  Q  L  D  R  I  F  S  V  M  G  F  P  A  D  K  D  W  E  D  I
     ATAAAAACAAGCAATCCCTTTCATCATGATCAACTGGATCGGATATTTAGTGTCATGGGGTTTCCTGCAGATAAAGACTGGGAAGATATT
```

FIG. 2A-2

```
       R   K   M   P   E   Y   P   T   L   Q   K   D   F   R   R   T   T   Y   A   N   S   S   L   I   K   Y   M   E   K   H
271    AGAAAGATGCCAGAATATCCCACACTTCAAAAGACTTTAGAAGAACTTATGCCAACAGTAGCCTCATAAGTACATGGAGAAACAC

K   V   K   P   D   S   K   V   F   L   L   Q   K   L   L   T   M   D   P   T   K   R   I   T   S   E   Q   A   L
301    AAGGTCAAGCCTGACAGCAAGTGTTCCTCTTGCTTCAGAACTCCTGACCATGGATCCAACCAAGAGAATTACCTCGGACAAGCTCTG

Q   D   P   Y   F   Q   E   D   P   L   P   T   L   D   V   F   A   G   C   Q   I   P   Y   P   K   R   E   F   L   N
331    CAGGATCCCTATTTTCAGGAGGACCCTTTGCCAACATTAGATGTATTTGCCGGCTGCCAGATTCCATACCCCAAACGAGAATTCCTTAAT

E   D   D   P   E   E   K   G   D   K   N   Q   Q   Q   H   Q   Q   T   A   P   P   Q   A   A
361    GAAGATGATCCTGAAGAAAAGGTGACAAGAATCAGCAACAACAGCAGCATCAGCAGCCCCACAGCCCCTCCACAGCAGGCAGCA

A   P   P   Q   A   P   P   P   Q   Q   N   S   T   Q   T   N   G   T   A   G   G   A   G   V   G   G   T   G
391    GCCCCTCCACAGGCGCCCCCACCACAGCAGAACAGCACCCAGACCAACGGCACCGCAGGTGGGGCTGGGGGTCGGGGGCACCGGA

A   G   L   Q   H   S   Q   D   S   L   N   Q   V   P   P   N   K   K   P   R   L   G   P   S   G   A   N   S   G
421    GCAGGGTTGCAGCACAGCCAGGACTCCAGCCTGAACCAGGTGCCTCCAAACAAGAAGCCACGGCTAGGGCCTTCAGGCGCAAACTCAGGT

G   P   V   M   P   S   D   Y   Q   H   S   S   R   L   N   Y   Q   S   S   V   Q   G   S   S   Q   S   Q   S   T
451    GGACCTGTGATGCCCTCGGATTATCAGCACTCCAGTTCTCGCCTGAATTACCAAAGCAGCGTTCAGGGATCCTCTCAGTCCCAGAGCACA

L   G   Y   S   S   S   Q   Q   S   S   Q   Y   H   P   S   H   Q   A   H   R   Y   *   502
481    CTTGGCTACTCTTCCTCGTCTCAGCAGAGCTCACAGTACCACCCATCTCACCAGGCCCACCGGTACTGACCAGCTCCCGTTGGGCCAGGC

CAGCCCAGCCCAGAGCACAGGCTCCAGCAATATGTCTGCATTGAAAAGAACCAAAAATGCAAACTATGCCATTAAAACTCATAC

ACATGGGAGGAAAACCTTATATACTGAGCATTGTGCAGGACTGTCTTCTTTATTGACTTAAAGAAGATTCTTGTGAAGTTTCCCC

AGCACCCCTTCCCTGCATGTGTTCCATTGTGACTTCTCTGATCTAATCCCAGCACTTCTGTAACCTTCTGTAACCTTCAGCATTTCTT

ACAGCCTAAGAAGAAAG
```

FIG. 2B-1

```
human   1   MDYDFKAKLAAERERVEDLFEYEGCKVGRGTYGHVYKARRKDGKDEKEYA    50
            ||||||||||||||||||||||||||||||||||||||||||||||||||
mouse   1   MDYDFKAKLAAERERVEDLFEYEGCKVGRGTYGHVYKARRKDGKDEKEYA    50 human  51   LKQIEGTGISMSACREIALLRELKHPNVIALQKVFLSHSDRKVWLLFDYA   100
            ||||||||||||||||||||:|||||||||||||||||||||||||||||
mouse  51   LKQIEGTGISMSACKEIALLRELNHPNVIALQKVFLSHSDRKVWLLFDYA   100 human 101   EHDLWHIIKFHRASKANKKPMQLPRSMVKSLLYQILDGIHYLHANWVLHR   150
            :||||||| |||||||||||||||:|||||||||||||||||||||||||
mouse 101   KHDLWHIINFHRASKANKKPMQLPKSMVKSLLYQILDGIHYLHANWVLHR   150 human 151   DLKPANILVMGEGPERGRVKIADMGFARLFNSPLKPLADLDPVVVTFWYR   200
            ||||||||||||||||||||||||||||||||||||||||||||||||||
mouse 151   DLKPANILVMGEGPERGRVKIADMGFARLFNSPLKPLADLDPVVVTFWYR   200 human 201   APELLLGARHYTKAIDIWAIGCIFAELLTSEPIFHCRQEDIKTSNPFHHD   250
            ||||||||||||||||||||||||||||||||||||||||||||||||||
mouse 201   APELLLGARHYTKAIDIWAIGCIFAELLTSEPIFHCRQEDIKTSNPFHHD   250 human 251   QLDRIFSVMGFPADKDWEDIRKMPEYPTLQKDFRRTTYANSSLIKYMEKH   300
            ||||||||||||||||||||||||||||||||||||||||||||||||||
mouse 251   QLDRIFSVMGFPADKDWEDIRKMPEYPTLQKDFRRTTYANSSLIKYMEKH   300
```

FIG. 2B-2

```
human  301 KVKPDSKVFLLLQKLLTMDPTKRITSEQALQDPYFQEDPLPTLDVFAGCQ 350
            |||||||||||||||||||||||||||||||||||||||||||||||||
mouse  301 KVKPDSKVFLLLQKLLTMDPTKRITSEQALQDPYFQEDPLPTLDVFAGCQ 350 human  351 IPYPKREFLNEDDPEEKGDKNQQQQQNHQQPTAPPQQAAAPPQAPPPQQ  400
            |||||||||||:||||||||| ||||:|||  ||||||  |||||||||
mouse  351 IPYPKREFLNEDEPEEKGDKNQPQQQNPHQQPAAPAQQTAAPPQAPPPQQ 400 human  401 NSTQTNGTAGGAGAGVGGTGAGLQHSQDSSLNQVPPNKKPRLGPSGANSG 450
            .:.|||||||| |||| ||||||||||||  ||||||||||:|||||||
mouse  401 SSAQTNGTAGGATAGGGGAGAGLQHSQDPGLNQVPPNKKPRIGPSGANSG 450 human  451 GPVMPSDYQHSSSRLNYQSSVQGSSQSTLGYSSSSQQSSQYHPSHQAH   500
            ||||||||||||||||||||||||||||||||  |||:|||||:||:|
mouse  451 GPVMPSDYQHSSSRLNYQSSVQGSSQSTLGY.SSSQQSTQYHSSHQTH   499 human  501 RY* 502
            ||
mouse  500 RY* 501
```

FIG. 2C-1

```
37691    1 MDYDFKAKLAAERERVEDLFEYEGCKVGRGTYGHVYKARRKDGKDEKEYA  50
           |||||||| ||  || |||||||||||||||||||||||| ||||:|:||
cdk8     1 MDYDFKVKLSSERERVEDLFEYEGCKVGRGTYGHVYKAKRKDGKDDKDYA  50

37691   51 LKQIEGTGISMSACREIALLRELKHPNVIALQKVFLSHSDRKVWLLFDYA 100
           ||||||||||||||||||||||||||||||| ||||||| |||||||||
cdk8    51 LKQIEGTGISMSACREIALLRELKHPNVISLQKVFLSHADRKVWLLFDYA 100

37691  101 EHDLWHIIKFHRASKANKKPMQLPRSMVKSLLYQILDGIHYLHANWVLHR 150
           |||||||||||||||||||||:||:||:||||||||||||||||||||||
cdk8   101 EHDLWHIIKFHRASKANKKPVQLPRGMVKSLLYQILDGIHYLHANWVLHR 150

37691  151 DLKPANILVMGEGPERGRVKIADMGFARLFNSPLKPLADLDPVVVTFWYR 200
           |||||||||||||||||||||||||||||||||||||||||||||||||
cdk8   151 DLKPANILVMGEGPERGRVKIADMGFARLFNSPLKPLADLDPVVVTFWYR 200

37691  201 APELLLGARHYTKAIDIWAIGCIFAELLTSEPIFHCRQEDIKTSNPFHHD 250
           |||||||||||||||||||||||||||||||||||||||||||||| ||
cdk8   201 APELLLGARHYTKAIDIWAIGCIFAELLTSEPIFHCRQEDIKTSNPYHHD 250
```

FIG. 2C-2

```
37691  251 QLDRIFSVMGFPADKDWEDIRKMPEYPTLQKDFRRTTYANSSLIKYMEKH 300
            ||||||:|||||||||||||:||||||||||||||||:|||||||||||
cdk8   251 QLDRIFNVMGFPADKDWEDIKKMPEHSTLMKDFRRNTYTNCSLIKYMEKH 300

37691  301 KVKPDSKVFLLLQKLLTMDPTKRITSEQALQDPYFQEDPLPTLDVFAGCQ 350
            |||||||.|||||||||||||:|||||||:|||||||:|||||||||||
cdk8   301 KVKPDSKAFHLLQKLLTMDPIKRITSEQAMQDPYFLEDPLPTSDVFAGCQ 350

37691  351 IPYPKREFLNEDDPEEKGDKNQQQQQNQHQQPTAPPQQAAAPPQAPPPQQ 400
            |||||||||.:.::|||||||||||...||                 QQ
cdk8   351 IPYPKREFLTEEEPDDKGDKKNQQQ..................... .QQ 377

37691  401 NSTQTNGTAGGAGAGVGGTGAGLQHSQDSSLNQVPPNKKPRLGPSGANSG 450
            ...:|||||:::    ::              |||.|::|:|:  ..||
cdk8   378 GNNHTNGTGHPGN................ QDSSHTQGPPLKKVRVVPPTTTSG 414

37691  451 GPVMPSDYQHSSSRLNYQSSVQGSSQSQSTLGYSSSSQQSSQYHPSHQAH 500
            |:|:|:||:||.:|.|:||  |::        |:   ||::||||:|||
cdk8   415 GLIMTSDYQRSNPHAAYPNPGSTSQPQSSMGYSATSQQPPQY..SHQTH 462

37691  501 RY* 502
            ||
cdk8   463 RY* 464
```

FIG. 3A murine DPK

```
                    TGGAGGAGGACTGAGTGGCGGCGCCCCGCGTCCGGTTTCTCTATGGGGAAGCAGACA
      M D Y D F K A K L A A E R E R V E D L F E Y E G C K V G R G
  1   ATGGATTATGATTTCAAGGCGAAGCTGGCGGCCGAGCGGGAGCGGGTGGAGGATCTGTTTGAGTACGAAGGTGCAAAGTGGGACGCGGC
      T Y G H V Y K A R R K D G K D E K E Y A L K Q I E G T G I S
 31   ACCTACGGGCATGTCTACAAGGCGAGGCGGAAAGATGAAAAGGAATATGCACTTAAGCAAATCGAAGGCACAGGAATATCT
      M S A C K E I A L L R E L N H H P N V I A L Q K V F L S H S D
 61   ATGTCGGCTTGTAAAGAGATTGCACTTTTGAGAGAACTGAACCACCCTAATGTGATCGCATTGCAAAAGGTGTTCCTTTCTCACAGCGAC
      R K V W L L F D Y A K H D L W H I I N F H R A S K A N K K P
 91   AGGAAGGTGTGGCTGCTGTTTGACTATGCAAAACATGACCTTTGGCATATTAATTTTCACCGTGCATCAAAAGCAAATAAAAAGCCC
      M Q L P K S M V K S L L Y Q I L D G I H Y L H A N W V L H R
121   ATGCAGTTACCAAAATCCATGGTTAAATCACTGTTGTACCAGATCCTCGATGGCATCCATTACCTCCACGCAAACTGGGTGCTCCACAGG
      D L K P A N I L V M G E G P E R G R V K I A D M G F A R L F
151   GACCTGAAACCAGCAAATATCCTAGTAATGGGAGAAGGTCCTGAAAGGGGAGAGTCAAAATAGCTGACATGGGTTTTGCCAGGTTATTC
      N S P L K P L A D L D P V V V T F W Y R A P E L L L G A R H
181   AATTCTCCCCTAAAGCCACTCGCAGATTTGGATCCAGTGGTTGTGACATTTTGGTATCGGGCTCCGGAACTTTTACTTGGTGCCAGGCAT
```

FIG. 3B

```
211  Y T K A I D I W A I G C I F A E L L T S E P I F H C R Q E D
     TACACAAAGGCCATTGACATCTGGGCAATAGGCTGCATATTTGCTGAACTCTTGACTTCAGAACCCATTTTCACTGTCGTCAGGAGGAT

241  I K T S N P F H H D Q L D R I F S V M G F P A D K D W E D I
     ATAAAAACAAGCAATCCTTTTCATCATGATCAGTTAGATCGAATATTTAGTGTCATGGGGTTTCCTGCAGATAAAGACTGGGAAGATATT

271  R K M P E Y P T L Q K D F R R T T Y A N S S L I K Y M E K H
     AGAAAAATGCCAGAGTACCCAACACTTCAGAAAGACTTTCGAAGAACAACGTACGCCAACAGCAGCCTCATAAAATACATGGAGAAGCAC

301  K V K P D S K V F L L L Q K L L T M D P T K R I T S E Q A L
     AAGGTCAAGCCTGACAGCAAAGTGTTCCTCCTGCTTCAGAAACTCCTCACCATGGATCCAACCAAGAGAATCACCTCAGAGCAGGCTCTG

331  Q D P Y F Q E D P L P T L D V F A G C Q I P Y P K R E F L N
     CAGGACCCTTACTTCCAGGAAGACCCCCTGCCAACATTAGATGTGTTCGCTGGCTGCCAGATTCCGTACCCCAAAAGAGAATTCCTTAAT

361  E D E P E E K G D K N Q P Q Q Q N P H Q Q P A A P A Q Q T A
     GAAGATGAACCAGAAGAGAAAGGTGACAAGAACCAGCCACAGCAGAACCCACATCAGCAACCTGCAGCCCCGCACAGCAGACAGCA

391  A P P Q A P P P Q Q S S A Q T N G T A G G G D G G G A G
     GCCCCCCCACAGGCTCCTCCACCACAGCAGAGCAGTGCCCAAACCAATGAACTGCTGGGGAGCCACTGCGGGGAGGGGGGCGCTGGA

421  A G L Q H S Q D P G L N Q V P P N K K P R I G P S G A N S G
     GCGGGGCTGCAGCACAGCCAGGACCCCGGCTGAATCAGGTGCCTCCAAACAAGAAGCCCCGGATTGGGCCTTCCGGTGCAAACTCAGGC
```

FIG. 3C

```
451  G  P  V  M  P  S  D  Y  Q  H  S  S  S  R  L  N  Y  Q  S  S  V  Q  G  S  S  Q  S  Q  S  T
     GGGCCCGTTATGCCGTCGGATTATCAGCATTCCAGTTCTCGCCCTGAATTACCAAAGCAGCGTACAGGGGTCCTCTCAGTCCCAGAGTACG

481  L  G  Y  S  S  S  Q  S  T  Q  Y  H  S  S  H  Q  T  H  R  Y  *   501
     CTAGGCTACTCTTCATCTCAACAGAGTACCCAGTACCACTCATCTCACCAGACCCACCGGTTGACCCACTCCCTCTGCTTGGCCTTGG

ACTCCAGCAGGGTGGTATTTGTGTTACAAAGACCCCCAGAATGAAGACTGACACCATGCAAAGTGCAGACCCTTGAGAGGAAACCTTTGC

ATGNTAAGTGTTTGAAGGACTAAGCTCTCTCTTCATTGACTAAAAGAGGATTCTTGTGAAGTGTCCCCGCCCTCTTCCCCCGCATGAT

TTCCTCTGTGACTTTCCTGATGAAGCCTCTGATCTACCCAGCACTTCTGCATCCTTCAGCAGTCTCTGAGGGAATTCTGTGTGCACCTTT

CTCACGCTGTAGCAATCATTATATAATTTATCTTTTCTTAGAGTTTCAATGTTGTAGGCACAGGGTTCCAGTGTGTATAGTTTTATACTTC

ATGAACTGATTTAGCAACACCAGTGAAATGCACCTTTTAAAGCACTCCACAGTCTCCACAGATAACTGCTCTGCTCTTGGAAGTCTTCA

AAAGAAACTGTTACTGTCCCAAAGTACTTTACTATTATGTTTTATTTATCTCTTTCAGGGAAGTGAAAGACACAGTGTGGACAGACGGT

GCCCACAACCAAAAACAGTGTAGGTCTTTGCAGCTACCTGCTATGCTATGAAAAACTGAAGTACTTGGTGATTTTTATATAATCATTCA

TGGGGAACTCAGTTCCCAGAATCATCATATTCTGAATAATATTCAGTAATTAAAATTATAATTTTAACTTCATGTAGCTAAGTCTACTTT
```

FIG. 3D

AAAGAGGTTTCAAGAGCTTTGACGGAATCCAGTCCTTTGGGACTCACCTGGGAAGTCTGAAGAGCCTGTTTCCTGCACTAGGACCTCAC

AAGGAGTCACGCTGATCAAAGCACGCTTCTTCCACGTGAAGGAAAAGCTTTTCCCATGTGTCTTCAGACGCTTCTCTCAAGGGGCTGC

TGGCTCTTCAGTCTCTTCACATCTGGTCAGCATGAGTAACTTTCTTCCATAATCAAGGATACTCAAATAGAAGCTTGTTCATTCATCTGC

AGGGTTTTCCATTGTGTGTACATTAAGCATAAAGTGACTATTTTAAAGCATGTTAAAATTTTAGGTTTCATTCATGTTGAAGTGTGT

ATTATGTATGCATAATTTGCTGTGTTACTGAGACTTAACGCTGTCAAGAATCTTTTGTATTGCACTGAATGCTTTCTTTTGCCCCTAGGAC

AAAAACCTTAATAATTGTGCCTAAGAACTATGGGCAGATAGTGTAAAGTAGATGAGGTGAATATTTGCATTCCATGATCTACGAATTAG

AGGGGAGTTCTATTTTAGCTACTTTTGAGGAACCCCCACCTCCAGAATCAAGAGGAAATGTAAAGGCTTAGAGCTCCCAGTGTAGTGCAG

GGGCAGAACACCTGTGTTCTGATGCTCCTAGCAGCCTTGTTTGCAATGTTTCTTGAGCTAGAAAAATAGCCAATTGTATATG

CAAACTATATGCATTTTAAAAAACTATTCTTGTGAACCTATCTACCTGGTTATGATACTCTGGGGTCCATATACAAGTAAAATAAGATT

TTTAGAAGCCAGTATACATTTGCACTATTGATGTGATACTGTAGCCAGCCAGGACCACACTGATTTCAGCATAAGGATGCTTATAAACA

FIG. 3E

GTAATAAAGGCTGTATGGTGCCATGCATACCAGGGCCGAAATGAAGTCATTGACATGTGACATGCTTCACTGGGAGGAATCTCTGACTG

TCTCCTTAGACTTTTTTTTTAATCCCTTATATTTTTAAATAAGAATCAGCCTTGTGCATAATGTCACTATCAATATAAAGTTCTGT

CCTGTGCCCTGGAGCCTCTTTGTCCAGGGCCACTGCTCCCTTCTCACAGGCTCAGTGCTCTGCTGGGAAGAAAACATAAAGAGTGGAGA

CATTCCTTATTGCAGCCAGTCCAGTGATCATAAGCTCCTGTGGGCCCCTGTGACTGACTTATAAATGCCCTGTGAGATGAA

GGTCCTTTGTTACTTCTCAACCCACTTGGATAAGTATGCTTCCGACTTTTATGGTAAACAGTGTTATGGGGAAGCAGGTCTGTGTCTGA

GCACTTGAGGAGAAAGCCAGTGATTAGCTGTCACAAAAGGCATCTATGCATATTTGAAATGTTCACAGCAGCCTTCAGCAGCAGTTGGGT

GGCCCTTGTGGACAGAGCATATTCTACTAAGTGGTTGTAGAGAATTACAATGAAAATAGAAGCTCTGTTCTTGCCCTCGAATGAGCTCAA

TTTAATAAAAGACATTAGCCCCTAAAAAAAAAAAAAAAAAAAAAAAA

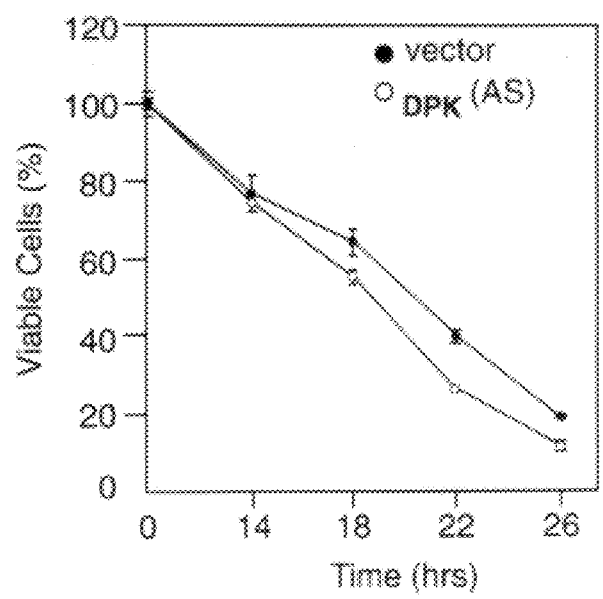

MAMMALIAN CELL DEATH PREVENTING KINASE, DPK

BACKGROUND

1. Field of the Invention

This invention relates to a novel polypeptide designated DPK-1 and related polypeptides that have an effect on apoptosis, to novel nucleic acid molecules encoding such polypeptides, and to other related aspects.

2. Description of Related Art

Normal development and tissue homeostasis in animals require the total cell numbers to be kept in an appropriate range. This is achieved by several highly regulated processes involving cell proliferation, survival, and elimination through programmed cell death (apoptosis). An imbalance between the rates of cell production and cell loss can result in serious human diseases such as cancer, disorders of the immune system, and neurodegenerations (reviewed by Rudin and Thompson, 1997).

Apoptosis appears to be an evolutionarily conserved, highly organized program of active cell destruction (reviewed by Miura and Yuan, 1996; Vaux and Strasser, 1996). In the nematode Caenorhabditis elegans, 14 genes involved in apoptosis have been identified. Among these, the CED-3 gene encodes a cysteine protease of the capsase family and is a key effector in the cell death pathway. The gene product of CED-4 appears to be an adaptor protein which activates CED-3 upon receiving apoptosis signals (Vaux, 1997; Jacobson, 1997). The CED-9 gene, a potent suppresser of programmed cell death, negatively regulates the activity of CED-3, probably through CED-4. In mammalian cells, multiple capsases have been identified and shown to be part of the cell death machinery (Henkart, 1996). The Bcl-2 proto-oncogene appears to be the prototype of mammalian homologs of CED-9 (Vaux et al, 1988; Vaux et al, 1992; Hengartner and Horvitz, 1994).

Other members of the Bcl-2 family consist of those (such as Bcl-XL) that are functionally similar to Bcl-2 which can block apoptosis; and others (Bax, for example) that have the opposite activity (Boise et al, 1993; Oltvai et al, 1993). Although the molecular mechanism is still unclear, recent evidence showed that Bcl-2 can block the release of cytochrome C from mitochondria (Yang et al, 1997; Kluck et al, 1997). In addition, Bcl-2 appears to directly inhibit capsase activation by binding to the mammalian CED-4 homolog (Zou et al, 1997). Other genes besides the Bcl-2 family have also been implicated in programmed cell death as well. For example, the transcription factors c-myc and NFkB may be involved in transducing signals for cell death or survival (Eskew et al, 1991; Evan et al, 1992; Hsu et al, 1995; Beg and Baldwin, 1996; Wang et al, 1996). The tumor suppresser gene p53, which is mutated in over 50% of human cancers, plays an essential role in radiation induced apoptosis in a wide variety of cell types (reviewed by Carson and Lois, 1995).

The cyclin-dependent kinases (CDKs) are a family of related serine/threonine kinases that are associated with and are activated by cyclins (Morgan, 1995). Although the CDKs were originally identified as key regulators of cell division, some newer members of the family clearly have functions outside of cell cycle control. In the budding yeast Saccharomyces cerevisiae, for example, the CDKs encoded by PHO85, KIN28, and SRB10 appear to be involved in transcriptional regulations (Hirst et al, 1994; Kattman et al, 1994; Liao et al, 1995). In mammalian cells, the CDK family currently consists of eight members. Of these, the CDK7/cyclin H complex has been shown to interact with the general transcription machinery (Feaver et al, 1994; Roy et al, 1994; Serizawa et al, 1995 Shiekhattar et al, 1995); and the primary target of CDK5 appears to be the neurofilament proteins (Hellmich et al, 1992; Shetty et al, 1993). The protein encoded by human CDK8 associates with cyclin C, an atypical cyclin which does not oscillate during cell cycle (Tassan et al, 1995). More recently, it was reported that Drosophila CDK8 can interact with and phosphorylate the large subunit of RNA polymerase II (Leclerc et al, 1996). Based on these results and the sequence similarities to the yeast SRB10/SRB11 pair, it was postulated that the CDK8/Cyclin C complex may play a role in transcriptional regulation.

Although a number of cell death related genes and proteins are now known, there remains a need to identify additional such genes and proteins and to determine their biological activity.

Accordingly, it is an object of the present invention to provide novel compounds that are associated with cell death in mammals.

It is a further object of the invention to provide a method of treating diseases associated with cell death such as those set forth herein.

These and other objects will be apparent to one of ordinary skill in the art from the present disclosure.

SUMMARY OF THE INVENTION

Programmed cell death (apoptosis) plays an essential role in development, differentiation and tissue homeostasis in vertebrates. To understand better the molecular events governing the process, screening for genes whose expression level is significantly altered during apoptosis by differential cDNA display was carried out.

One of the cDNA clones thus identified (death preventing kinase, DPK) appears to be a novel member of the CDK family kinases with significant homology to human CDK8, the latter having unknown functions. The DPK gene is highly conserved in evolution and the predicted amino acid sequences of the human and murine DPK are 96% identical. Like CDK8, the encoded protein is specifically associated with cyclin C. Additionally, the gene product appears to localize to the nucleus as assessed by immunofluorescence of the epitope-tagged protein.

In T cells, the DPK message is highly induced during programmed cell death. Furthermore, the expression of the gene from a constitutive promoter leads to increased resistance to apoptosis in a factor dependent T cell clone. Conversely, expression of the antisense message significantly accelerated cell death after growth factor deprivation. Taken together, the results indicate that DPK can protect cells from programmed death, similar to the well known Bcl-2 family of proteins. To the knowledge of the inventor, DPK is the first example of a cdk-like kinase playing an important role in the regulation of apoptosis.

Therefore, in summary, the herein described invention is based on the isolation and characterization of a novel CDK-like kinase (referred to herein as "DPK", for death-preventing kinase). DPK has been found to be upregulated in dying cells, such as T cells cultured in the absence of stimuli. The gene is highly conserved between mouse and human and is closely related to CDK8 in sequence. The encoded protein associates specifically with cyclin C in vitro and appears to localize to the nuclei. Ectopic expression of DPK in an IL-2 dependent murine T cell clone conferred significant protection from growth factor withdrawal induced apoptosis. Furthermore, expression of the antisense DPK message renders the cells more susceptible to apoptosis. In humans, high levels of expression of DPK are detected in brain, heart, and a few other tissues. These results suggest that the function of DPK in normal physiological conditions may be to protect cells from unintended, accidental death.

The present invention embodies various aspects, as set forth in the following:

In a first embodiment, the present invention provides a nucleic acid molecule encoding a polypeptide selected from the group consisting of:

(a) the nucleic acid molecule of SEQ ID NO:1;

(b) a nucleic acid molecule encoding the polypeptide of SEQ ID NO:2 or a biologically active fragment thereof;

(c) a nucleic acid molecule that encodes a polypeptide that is at least 85 percent identical to the polypeptide of SEQ ID NO:2;

(d) a nucleic acid molecule that hybridizes under stringent conditions to any of (a)–(c) above; and (e) a nucleic acid molecule that is the complement of any of (a)–(d) above.

In another embodiment, the present invention provides a nucleic acid molecule encoding a polypeptide selected from the group consisting of (a') the nucleic acid molecule of SEQ ID NO:3;

(b') a nucleic acid molecule encoding the polypeptide of SEQ ID NO:4 or a biologically active fragment thereof;

(c') a nucleic acid molecule that encodes a polypeptide that is at least 85 percent identical to the polypeptide of SEQ ID NO:4;

(d') a nucleic acid molecule that hybridizes under stringent conditions to any of (a')–(c') above; and (e') a nucleic acid molecule that is the complement of any of (a')–(d') above.

In another embodiment, the invention provides vectors comprising these nucleic acid molecules, and host cells, either prokaryotic or eukaryotic, comprising the vectors.

The invention further provides a DPK polypeptide selected from the group consisting of:

(a) the polypeptide of SEQ ID NO:2;

(b) a polypeptide that is at least 85 percent identical to the polypeptide of (a); and (c) a biologically active fragment of any of (a)–(b).

The invention further provides a DPK polypeptide selected from the group consisting of:

(a') the polypeptide of SEQ ID NO:4;

(b') a polypeptide that is at least 85 percent identical to the polypeptide of (a'); and (c') a biologically active fragment of any of (a')–(b').

Optionally, the DPK polypeptide may or may not have an amino terminal methionine.

In another embodiment, the invention provides a process for producing a DPK polypeptide, wherein the polypeptide may be SEQ ID NO:2 or SEQ ID NO:4 or a biologically active fragment thereof, and wherein the process comprises:

(a) expressing a polypeptide encoded by a DPK nucleic acid molecule in a suitable host; and (b) isolating the polypeptide.

The invention further provides anti-DPK antibodies.

These additional related aspects of the invention will be better appreciated by referring to the figures which are described in the following section.

BRIEF DESCRIPTION OF THE DRAWINGS

FIGS. 1(a and b) depict a gel showing induction of DPK expression in primary mouse T cells undergoing apoptosis. T cells isolated from mouse peripheral lymph nodes were cultured overnight with ("+" lanes) or without ("−" lanes) PMA/ionomycin stimulation. Total RNA was prepared and then analyzed by (1a) differential cDNA display in duplicates; the band that corresponds to part of the DPK cDNA is marked by the asterisk; and (1b) Northern hybridization using the mouse DPK or β-actin probe as indicated.

FIGS. 2 (a–c) shows (2a) the nucleic acid sequence of the cDNA encoding a preferred human DPK protein (human DPK-1) and the associated protein sequence (SEQ ID NOS:1 and 2), (2b) a comparison of the human and murine DPK protein sequences (SEQ ID NOS:2 and 4, respectively), and (2c) a comparison between human DPK-1 protein sequence (SEQ ID NO: 2) with human CDK-8 protein sequence (SEQ ID NO: 5). Note that at the amino acid level, human DPK-1 is 96% identical to the mouse gene and approximately 88% similar to human CDK-8.

FIG. 3 shows the nucleic acid sequence of the cDNA encoding a preferred murine DPK protein (murine DPK-1) and the associated protein sequence (SEQ ID NOS:3 and 4).

DETAILED DESCRIPTION OF THE INVENTION

Figure 4:
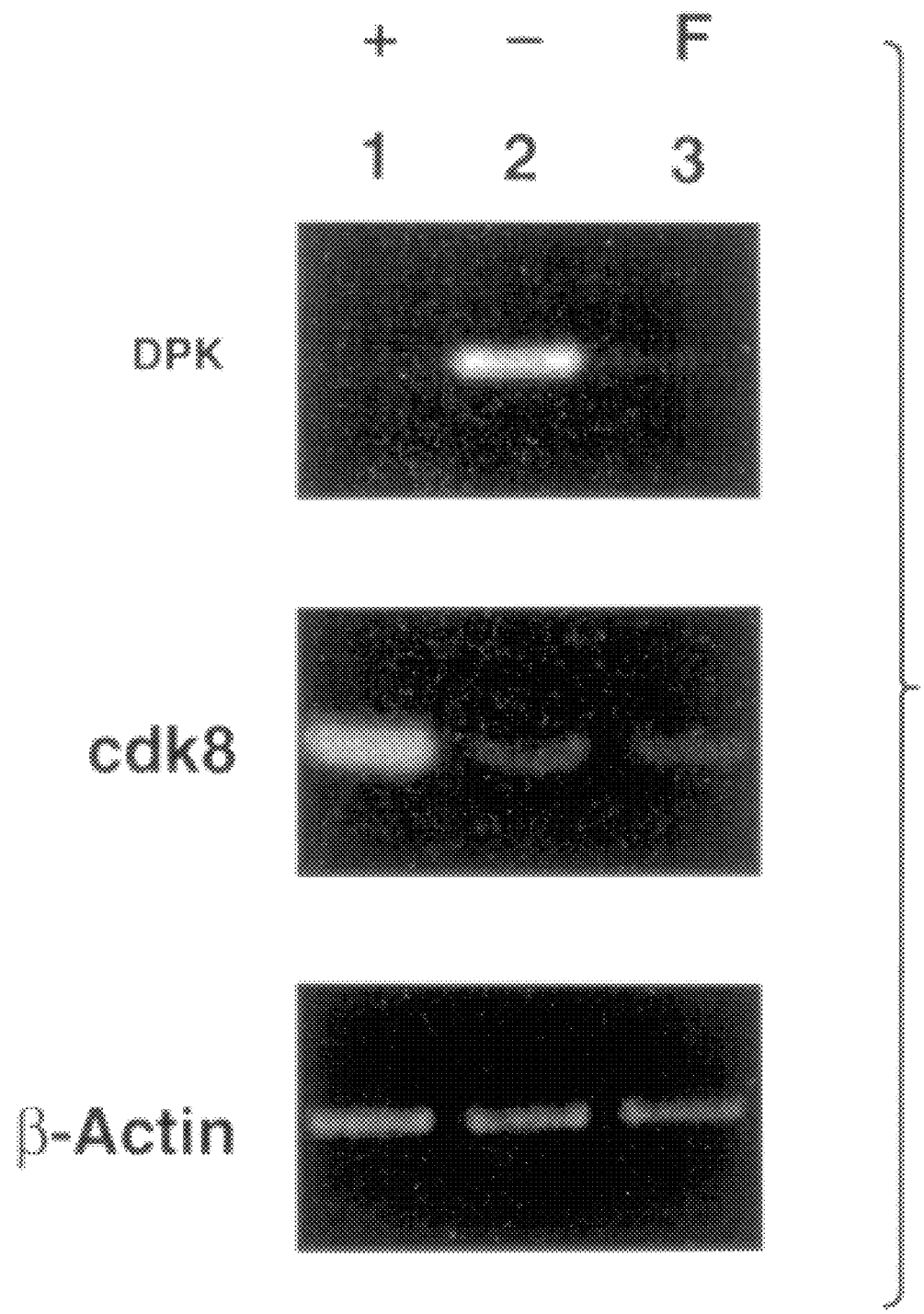
FIG. 4 depicts the analyses of DPK and CDK8 expression in human peripheral blood T cells. T cells were enriched from normal human peripheral blood mononuclear cells by panning. Total RNA was prepared from T cells cultured overnight with ("+") or without ("−") PMA/Ionomycin. As a control for nondying and nondividing T cells, RNA was also prepared from freshly isolated T cells without culturing (lane "F"). RT-PCR analyses were performed with gene-specific primers. The amount of template in each PCR reaction was adjusted to give rise to equal amount of β-actin.

Included in the scope of this invention are DPK polypeptides such as the polypeptides of SEQ ID NO:2 (human DPK-1) or SEQ ID NO: 4 (murine DPK-1), and related biologically active polypeptide fragments and derivatives thereof. Further included within the scope of the present invention are nucleic acid molecules that encode these polypeptides, methods for preparing the polypeptides, and other related aspects.

I. DPK-1 Proteins/Polypeptides, Fragments and Derivatives Thereof

The term "DPK protein" or "DPK polypeptide" as used herein refers to any protein or polypeptide having the properties described herein for DPK. The DPK polypeptide may or may not have an amino terminal methionine, depending, for example, on the manner in which it is prepared. By way of illustration, DPK protein or DPK polypeptide refers to:

(1) an amino acid sequence encoded by DPK nucleic acid molecules as defined in any of the following items:
 (a) the nucleic acid molecules of SEQ ID NOS:1 or 3;
 (b) nucleic acid molecules encoding the polypeptides of SEQ ID NOS:2 or 4, or biologically active fragments thereof;
 (c) nucleic acid molecules encoding polypeptides that are at least 85 percent identical to the polypeptides of SEQ ID NOS:2 or 4;
 (d) nucleic acid molecules that hybridize under stringent conditions to any of (a)–(c) above; and
 (e) nucleic acid molecules that are the complement of any of (a)–(d) above.

(2) naturally occurring allelic variants of the DPK gene (e.g., the human and murine DPK-1 genes; SEQ ID NOS: 1 and 3, respectively) which result in one or more amino acid substitutions, deletions, and/or insertions as compared to the DPK-1 polypeptides of SEQ ID NO:2 or SEQ ID NO: 4, and/or (3) chemically modified derivatives as well as nucleic acid and or amino acid sequence variants thereof as provided for herein.

The DPK polypeptides that have use in practicing the present invention may be naturally occurring full length polypeptides, or truncated polypeptides or peptides (i.e, "fragments").

The polypeptides may be in mature form or they may be attached to a signal peptide, e.g., a heterologous signal peptide (native DPK does not appear to have a signal peptide).

The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring DPK polypeptides (i.e., may contain one or more amino acid deletions, insertions, and/or substitutions as compared with naturally occurring DPK, e.g., DPK-1).

As used herein, the term "DPK fragment" refers to a peptide or polypeptide that is less than the full length amino acid sequence of naturally occurring DPK protein but has qualitatively a substantially similar type of biological activity as DPK polypeptide or DPK protein described above. Such a fragment may be truncated at the amino terminus, the carboxy terminus, or both, and may be chemically modified. Such DPK fragments may be prepared with or without an amino terminal methionine. The activity of the fragments may be greater than, the same as, or less than the full-length (mature) DPK polypeptide. Preferably, the activity of the fragment is ≧50%, more preferably ≧65%, most preferably ≧80%, of the activity of the full-length polypeptide, as measured by a standard activity assay, such as those set forth in the Examples section herein. Some exemplary fragments of this invention include the polypeptides wherein from 1 to 20 amino acids are removed from either the C-terminus, the N-terminus, or both termini, of the DPK polypeptide.

As used herein, the term "DPK derivative" or "DPK variant" refers to a DPK polypeptide, protein, or fragment that 1) has been chemically modified, as for example, by addition of one or more polyethylene glycol molecules, sugars, phosphates, or other such molecules not naturally attached to wild-type DPK polypeptide, and/or 2) contains one or more nucleic acid or amino acid sequence substitutions, deletions, and/or insertions as compared to the DPK amino acid sequence, such as those set forth in FIG. 2a (human) or FIG. 3 (murine).

As used herein, the terms "biologically active polypeptide" and "biologically active fragment" refer to a peptide or polypeptide in accordance with the above description for DPK wherein the DPK acts as a kinase that is capable of prolonging survival of cells (e.g., T-cells)

Fragments and/or derivatives of DPK that are not themselves active in activity assays may be useful as modulators (e.g., inhibitors or stimulants) of the DPK receptors in vitro or in vivo, or to prepare antibodies to DPK polypeptides.

The amino acid variants of DPK of this invention preferably are at least 85% identical to either SEQ ID NO: 2 or SEQ ID NO: 4, more preferably at least about 90% identical, even more preferably at least about 95% identical.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a predetermined portion of one or both sequences). Each computer program provides a "default" opening penalty and a "default" gap penalty, and a scoring matrix such as PAM 250. A standard scoring matrix (see Dayhoff et al., in: *Atlas of Protein Sequence and Structure*, vol. 5, supp.3 [1978]) can be used in conjunction with the computer program. The percent identity can then be calculated using an algorithm contained in a program such as FASTA as:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 85 percent identical will typically have one or more amino acid substitutions, deletions, and/or insertions as compared with wild type DPK. Usually, the substitutions will be conservative so as to have little or no effect on the overall net charge, polarity, or hydrophobicity of the protein but optionally may increase the activity of DPK. Conservative substitutions are set forth in Table I below.

TABLE I

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The invention also encompasses species homologs of DPK; for example, DPK homologs from a mammalian species such as dog, cat, mouse, rat, monkey, horse, pig, goat, rabbit, sheep and the like are contemplated in addition to human. The sequence of the exemplary murine protein, DPK-1, is provided as SEQ ID NO: 4.

The invention further encompasses chimeric polypeptides, i.e., DPK attached to all or a portion of another polypeptide. Preferably the chimeric polypeptide comprises DPK attached to all or a portion of another factor. The polypeptides may be attached N to C terminus, C to C terminus, or N to N terminus. They may be attached directly, or they may be connected via a linker, such as a polyamino acid linker (e.g., poly-Gly).

II. Nucleic Acids

As used herein, the term "DPK" when used to describe a nucleic acid molecule refers to a nucleic acid molecule or fragment thereof, as set forth above.

The term "stringent conditions" refers to hybridization and washing under conditions that permit only binding of a nucleic acid molecule such as an oligonucleotide or cDNA molecule probe to highly homologous sequences. One strin-gent wash solution is 0.015 M NaCl, 0.005 M NaCitrate, and 0.1 percent SDS used at a temperature of 55–65° C. Another stringent wash solution is 0.2×SSC and 0.1 percent SDS used at a temperature of between 50–65° C. Where oligonucleotide probes are used to screen cDNA or genomic libraries, the following stringent washing conditions may be used. One protocol uses 6×SSC with 0.05 percent sodium pyrophosphate at a temperature of 35–62° C., depending on the length of the oligonucleotide probe. For example, 14 base pair probes are washed at 35–40° C., 17 base pair probes are washed at 45–50° C., 20 base pair probes are washed at 52–57° C., and 23 base pair probes are washed at 57–630C. The temperature can be increased 2–3° C. where the background non-specific binding appears high. A second protocol utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45–50° C.

DPK nucleic acid molecules, fragments, and/or derivatives that do not themselves encode polypeptides that are active in activity assays may be useful as hybridization probes in diagnostic assays to test, either qualitatively or quantitatively, for the presence of DPK DNA or RNA in mammalian tissue or bodily fluid samples.

DPK nucleic acid molecules encoding DPK polypeptides attached to a heterogeneous signal peptide and/or to a chimeric polypeptide as described herein above are also included within the scope of this invention.

III. Methods for Preparing DPK Polypeptides

A. Recombinant Methods

The full length DPK polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, N.Y. [1994]). A gene or CDNA encoding the DPK protein or fragment thereof may be obtained for example by screening a genomic or cDNA library, or by PCR amplification. Alternatively, a gene encoding the DPK polypeptide or fragment may be prepared by chemical synthesis using methods well known to the skilled artisan such as those described by Engels et al.(*Angew. Chem. Intl. Ed.,* 28: 716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the DPK polypeptide will be several hundred nucleotides in length. Nucleic acids larger than about 100 nucleotides can be synthesized as several fragments using these methods. The fragments can then be ligated together to form the full length DPK polypeptide. Usually, the DNA fragment encoding the amino terminus of the polypeptide will have an ATG, which encodes a methionine residue. This methionine may or may not be present on the mature form of the DPK polypeptide, depending on whether the polypeptide produced in the host cell is secreted from that cell.

In some cases, it may be desirable to prepare nucleic acid and/or amino acid variants of naturally occurring DPK. Nucleic acid variants (wherein one or more nucleotides are designed to differ from the wildtype or naturally occurring DPK) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce DPK. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s) on DPK, or those designed to delete an existing glycosylation and/or phosphorylation site(s) on DPK.

The DPK gene or cDNA can be inserted into an appropriate expression vector for expression in a host cell. The vector is selected to be functional in the particular host cell employed (i.e., the vector is compatible with the host cell machinery such that amplification of the DPK gene and/or expression of the gene can occur). The DPK polypeptide or fragment thereof may be amplified/expressed in prokaryotic, yeast, insect (baculovirus systems) and/or eukaryotic host cells. Selection of the host cell will depend at least in part on whether the DPK polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the DPK polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the DPK coding sequence that encodes polyhis (such as hexaHis) or another small immunogenic sequence. This tag will be expressed along with the protein, and can serve as an affinity tag for purification of the DPK polypeptide from the host cell. Optionally, the tag can subsequently be removed from the purified DPK polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native DPK 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the DPK 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the DPK polypeptide. If the vector of choice does not contain an origin of replication site, one may be chemically synthesized based on a known sequence, and ligated into the vector.

The transcription termination element is typically located 3' of the end of the DPK polypeptide coding sequence and serves to terminate transcription of the DPK polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the DPK polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In many cases, transcription of the DPK polypeptide is increased by the presence of one or more introns on the vector; this is particularly true where DPK is produced in eukaryotic host cells, especially mammalian host cells. The introns used may be naturally occurring within the DPK nucleic acid sequence, especially where the DPK sequence used is a full length genomic sequence or a fragment thereof. Where the intron is not naturally occurring within the DPK DNA sequence (as for most cDNAs), the intron(s) may be obtained from another source. The position of the intron with respect to the 5' flanking sequence and the DPK coding sequence is important, as the intron must be transcribed to be effective. As such, where the DPK nucleic acid sequence is a cDNA sequence, the preferred position for the intron is 3' to the transcription start site, and 5' to the polyA transcription termination sequence. Preferably for DPK cDNAs, the intron will be located on one side or the other (i.e., 5' or 3') of the DPK coding sequence such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vector such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and/or mammalian host cells. Such vectors include, inter alia, pCRII (Invitrogen Company, San Diego, Calif.), pBSII (Stratagene Company, Lajolla, Calif.), and pETL (BlueBacII; Invitrogen).

After the vector has been constructed and a DPK nucleic acid has been inserted into the proper site of the vector, the completed vector may be inserted into a suitable host cell for amplification and/or DPK polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize DPK protein which can subsequently be collected from the culture medium (if the host cell secretes it into the medium) or directly from the host cell producing it (if it is not secreted). After collection, the DPK protein can be purified using methods such as molecular sieve chromatography, affinity chromatography, and the like.

Selection of the host cell will depend in part on whether the DPK protein is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize biologically active DPK, the DPK may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DHI10, and MC1061) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where desired, insect cells may be utilized as host cells in the method of the present invention (Miller et al., *Genetic Engineering* 8: 277–298 [1986]).

Insertion (also referred to as "transformation" or "transfection") of the vector into the selected host cell may be accomplished using such methods as calcium phosphate, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of DPK polypeptide produced in the host cell can be evaluated using standard methods known in the art. Such methods include, without limitation, Western blot analysis, SDS-polyacrylamide gel electrophoresis, nondenaturing gel electrophoresis, HPLC separation, immunoprecipitation, and/or activity assays such as kinase assays.

If the DPK polypeptide has been designed to be secreted from the host cells, the majority of polypeptide may be found in the cell culture medium. Polypeptides prepared in this way will typically not possess an amino terminal methionine, as it is removed during secretion from the cell. If however, the DPK polypeptide is not secreted from the host cells, it will be present in the cytoplasm (for eukaryotic, gram positive bacteria, and insect host cells) or in the periplasm (for gram negative bacteria host cells) and may have an amino terminal methionine.

For intracellular DPK protein, the host cells are typically first disrupted mechanically or osmotically to release the cytoplasmic contents into a buffered solution. DPK polypeptide can then be isolated from this solution.

Purification of DPK polypeptide from solution can be accomplished using a variety of techniques. If the polypeptide has been synthesized such that it contains a tag such as Hexahistidine (DPK/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing DPK). For example, polyhistidine binds with great affinity and specificity to nickel, thus an affinity column of nickel (such as the Qiagen nickel columns) can be used for purification of DPK/polyHis. (See for example, Ausubel et al., eds., *Current Protocols in Molecular Biology*, Section 10.11.8, John Wiley & Sons, New York [1993]).

Where the DPK polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

If it is anticipated that the DPK polypeptide will be found primarily in the periplasmic space of the bacteria or the cytoplasm of eukaryotic cells, the contents of the periplasm or cytoplasm, including inclusion bodies (e.g., gram-negative bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the DPK polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The DPK polypeptide in its now soluble form can then be analyzed using gel electrophoresis, immunoprecipitation or the like. If it is desired to isolate the DPK polypeptide, isolation may be accomplished using standard methods such as those set forth below and in Marston et al. (*Meth. Enz.*, 182: 264–275 [1990]).

If DPK polypeptide inclusion bodies are not formed to a significant degree in the periplasm of the host cell, the DPK polypeptide will be found primarily in the supernatant after centrifugation of the cell homogenate, and the DPK polypeptide can be isolated from the supernatant using methods such as those set forth below.

In those situations where it is preferable to partially or completely isolate the DPK polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

B. Chemical Synthesis Methods

In addition to preparing and purifying DPK polypeptide using recombinant DNA techniques, the DPK polypeptides, fragments, and/or derivatives thereof may be prepared by chemical synthesis methods (such as solid phase peptide synthesis) using methods known in the art such as those set forth by Merrifield et al., (*J. Am. Chem. Soc.*, 85: 2149 [1964]), Houghten et al. (*Proc Natl Acad. Sci. USA*, 82: 5132 [1985]), and Stewart and Young (Solid Phase Peptide Synthesis, Pierce Chem Co, Rockford, Ill. [1984]). Such polypeptides may be synthesized with or without a methionine on the amino terminus. Chemically synthesized DPK polypeptides or fragments may be oxidized using methods set forth in these references to form disulfide bridges. The DPK polypeptides or fragments may be employed as biologically active or immunological substitutes for natural, purified DPK polypeptides in therapeutic and immunological processes.

IV. Chemically Modified DPK Derivatives

Chemically modified DPK compositions (i.e., "derivatives") where the DPK polypeptide is linked to a polymer ("DPK-polymers") are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of DPK-polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1-C10 alkoxy or aryloxy derivatives thereof (see U.S. Pat. No. 5,252,714).

Pegylation of DPK may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable conditions used to react a biologically active substance with an activated polymer molecule. Methods for preparing pegylated DPK will generally comprise the steps of (a) reacting a DPK polypeptide with polyethylene glycol (such as a reactive ester or aldehyde derivative of PEG) under conditions whereby DPK becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Generally, conditions which may be alleviated or modulated by administration of the present polymer/DPK include those described herein for DPK molecules in general. However, the polymer/DPK molecules disclosed herein may have additional activities, enhanced or reduced activities, or other characteristics, as compared to the non-derivatized molecules.

V. Combinations

The DPK polypeptides and fragments thereof, whether or not chemically modified, may be employed alone, or in combination with other pharmaceutical compositions such as, for example, cytokines, interferons, interleukins, growth factors, antibiotics, anti-inflammatories, chemotherapeutic agents, in the treatment of various disorders, such as cancer, immunodeficiency, and neurodegeneration.

VI. Antibodies

The DPK polypeptides, fragments, and/or derivatives thereof may be used to prepare antibodies generated by standard methods. Thus, antibodies that react with the DPK polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will be "humanized", i.e., prepared so as to prevent or minimize an immune reaction to the antibody when administered to a patient. The antibody fragment may be any fragment that is reactive with the DPK of the present invention, such as, Fab, Fab', etc. Also provided by this invention are the hybridomas generated by presenting DPK or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human DPK polypeptide of the present invention are also encompassed by this invention.

The antibodies may be used therapeutically, such as to inhibit binding of DPK to its substrates. The antibodies may further be used for in vivo and in vitro diagnostic purposes, such as in labeled form to detect the presence of the DPK polypeptide in a tissue.

Antibodies against DPK-1, particularly human, and active fragments thereof, are preferred.

VII. Therapeutic Compositions and Administration Thereof

As used herein, the terms "effective amount" and "therapeutically effective amount" refer to the amount of DPK necessary to support one or more biological activities of DPK as set forth above.

Therapeutic compositions for treating various disorders or diseases associated with cell death are within the scope of the present invention. It should be noted that based on current data, it appears that for DPK itself to carry out its normal function, it should be delivered to the nuclear region of a cell, which may be difficult to achieve with standard pharmaceutical delivery methods. Nevertheless, there may be physiological mechanisms whereby DPK has therapeutic utility upon direct administration to patients suffering from various conditions. Such conditions include, for example, immunodeficiency disorders (e.g., AIDS), stroke, heart attack, head trauma, and neurodegenerative diseases (e.g., Parkinson's disease and Alzheimer's disease).

Such compositions may comprise a therapeutically effective amount of a DPK polypeptide, a fragment thereof (either of which may be chemically modified) or a modulator of DPK activity, (collectively, a "DPK therapeutic compound") in admixture with a pharmaceutically acceptable carrier. The carrier material may be water for injection, preferably supplemented with other materials common in solutions for administration to mammals. Typically, a DPK therapeutic compound will be administered in the form of a composition comprising the DPK therapeutic compound in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. An exemplary composition comprises citrate buffer of about pH 4.0–4.5, which may further include NaCl.

The DPK compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of DPK compositions useful for practicing the present invention may be prepared for storage by mixing the selected composition having the desired degree of purity with optional physiologically acceptable carriers, excipients, or stabilizers (*Remington's Pharmaceutical Sciences,* 18th edition, A.R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids;

antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The DPK composition to be used for in vivo administration must be sterile. This is readily accomplished by filtration through sterile filtration membranes. Where the DPK composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, DPK may be administered locally via implantation into the affected area of a membrane, sponge, or other appropriate material on to which DPK polypeptide has been absorbed.

Where an implantation device is used, the device may be implanted into any suitable tissue or organ, such as, for example, into a cerebral ventricle or into brain parenchyma, and delivery of DPK may be directly through the device via bolus or continuous administration, or via a catheter using continuous infusion.

DPK polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamine (Sidman et al, *Biopolymers,* 22: 547–556 [1983]), poly (2-hydroxyethyl-methacrylate) (Langer et al., *J. Biomed. Mater. Res.,* 15: 167–277 [1981] and Langer, Chem. Tech., 12: 98–105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA,* 82: 3688–3692 [1985]; Hwang et al., *Proc. Natl. Acad. Sci. USA,* 77: 4030–4034 [1980]; EP 52,322; EP 36,676; EP 88,046; EP 143,949).

In some cases, it may be desirable to use DPK compositions in an ex vivo manner, i.e., to treat cells or tissues that have been removed from the patient and are then subsequently implanted back into the patient.

In other cases, DPK may be delivered through implanting into patients certain cells that have been genetically engineered to express and secrete DPK polypeptide. Such cells may be animal or human cells, and may be derived from the patient's own tissue or from another source, either human or non-human. Optionally, the cells may be immortalized. The cells may be implanted into the brain, adrenal gland or into other suitable body tissues or organs of the patient.

In certain situations, it may be desirable to use gene therapy methods for administration of DPK to patients suffering from certimmunological, alogical, immunological, and other) disorders. In these situations, genomic DNA, cDNA, and/or synthetic DNA encoding DPK or a fragment or variant thereof may be operably linked to a constitutive or inducible promoter that is active in the tissue into which the composition will be injected. This DPK DNA construct, either inserted into a vector, or alone without a vector, can be injected or otherwise administered directly into brain, heart, or other tissue, either neuronal or non-neuronal.

An effective amount of the DPK composition(s) to be employed therapeutically will depend, for example, upon the therapeutic objectives such as the indication for which DPK is being used, the route of administration, and the condition of the patient. Accordingly, it will be necessary for the therapist to titer the dosage and modify the route of administration as required to obtain the optimal therapeutic effect. A typical daily dosage may range from about 0.1 $\mu$g/kg to up to 10 mg/kg or more, depending on the factors mentioned above. Typically, a clinician will administer the DPK composition until a dosage is reached that achieves the desired effect. The DPK composition may therefore be administered as a single dose, or as two or more doses (which may or may not contain the same amount of DPK) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

VIII. Diagnostic Uses

DPK RNA and protein levels may be measured for diagnostic purposes. Such levels may be indicative of the presence or progression of various diseases, such as cancer, immunodeficiency disorders (e.g., AIDS), stroke, heart attack, head trauma, and neurodegenerative diseases (e.g., Parkinson's disease and Alzheimer's disease), preferably cancer. For example, increased levels of DPK RNA have been detected in some tumor samples (colon cancer).

IX. Conditions to be Treated with DPK

The DPK proteins, fragments and/or derivatives thereof may be utilized to treat diseases and disorders associated with alterations in cell proliferation/death which may benefit from exposure to DPK or anti-DPK antibodies.

DPK protein and/or fragments or derivatives thereof, may be used directly to treat patients suffering from cancer, immunodeficiency disorders (e.g., AIDS), stroke, heart attack, head trauma, and neurodegenerative diseases (e.g., Parkinson's disease and Alzheimer's disease).

X. Modulators of DPK Levels

In some situations, such as treatment of cancer, it may be desirable to inhibit or significantly decrease the level of DPK activity or expression. Compounds that inhibit DPK activity/expression could be administered either in an ex vivo manner, or in an in vivo manner by local or iv injection, or by oral delivery, implantation device, or the like. Exemplary inhibitory compounds are antisense oligonucleotides against DPK genes, antibodies against DPK proteins, and small molecule inhibitors of DPK expression or activity.

In other situations, such as in cases wherein cell survival is desirably increased (e.g., AIDS, stroke, neurodegenerative diseases, head/brain trauma, and heart attack, etc.), it may be desirable to enhance or significantly increase the level of DPK activity or expression. Compounds that increase DPK activity or expression could be administered either in an ex vivo manner, or in an in vivo manner by local or iv injection, or by oral delivery, implantation device, or the like.

The assays described below provide examples of methods useful for identifying compounds that could inhibit or enhance DPK activity.

For ease of reading, the following definition is used herein for describing the assays:

"Test molecule(s)" refers to the molecule(s) that is under evaluation as a modulator of DPK, e.g., by virtue of its potential ability to block or enhance the kinase activity of DPK.

Several types of in vitro assays using purified protein may be conducted to identify those compounds that affect DPK function. Such affect may be accomplished by a compound that typically inhibits or enhances the kinase activity of DPK.

In one assay, recombinant cyclin C and purified DPK protein or a fragment thereof (prepared for example using methods described above) can be added to the bottom of the wells of a microtiter plate. A model substrate for DPK, $\gamma$-$^{32}$P ATP, as well as the test molecule(s) can then be added either one at a time or simultaneously to the wells. After incubation, the unincorporated $^{32}$P can be removed using a commercially available device such as Pierce Phosphocellulose units. Phosphorylation of the substrate can be determined by scintillation counting. Typically, the molecule will be tested over a range of concentrations, and a series of control "wells" lacking one or more elements of the test assays can be used for accuracy in evaluating the results. A variation of this assay involves colorimetric measurement of DPK kinase activity using a dye-labeled model substrate and affinity membrane to separate the phosphorylated and unphosphorylated substrate, similar to the PKA assay system sold by Pierce.

In some cases, it may be desirable to evaluate two or more test molecules together for use in decreasing or increasing DPK activity. In these cases, the assays set forth above can be readily modified by adding such additional test molecule (s) either simultaneously with, or subsequently to, the first test molecule. The remainder of steps in the assay can be as set forth above.

XI. Transgenic Mammals

Also included within the scope of the present invention are non-human mammals such as mice, rats, rabbits, goats, or sheep in which the gene (or genes) encoding the human equivalent of DPK (e.g., DPK-1) has been disrupted ("knocked out") such that the level of expression of this gene is significantly decreased or completely abolished. Such mammals may be prepared using techniques and methods such as those described in U.S. Pat. No. 5,557,032. The present invention further includes non-human mammals such as mice, rats, rabbits, goats, or sheep in which the gene (or genes) encoding the DPK (either the native form of DPK for the mammal or a heterologous DPK gene) is over expressed by the mammal, thereby creating a "transgenic" mammal. Such transgenic mammals may be prepared using well known methods such as those described in U.S. Pat. No. 5,489,743 and PCT patent application no. W094/28122, published Dec. 8, 1994.

The following examples are intended for illustration purposes only, and should not be construed as limiting the scope of the invention in any way.

EXAMPLES

Materials and Methods

Cells and Culture Conditions

Primary mouse T cells were isolated as follows: lymph nodes, which consist of 80% T cells, were collected from 10–12 week old female Balb/c mice killed by $CO_2$ asphyxiation and single cell suspensions were prepared. After removing dead cells by spinning through Lympholyte-M (Cedarlane Laboratories), the B cells (sIg+) were removed by panning twice on petri dishes coated with saturating amount of goat-anti-mouse IgG (KPL). The remaining cells were then cultured in complete DMEM+10% FBS overnight. For cell activation, 10 ng/ml PMA (Sigma) and 1 mM ionomycin (Calbiochem) were added to the media. The proper activation was ascertained by RT-PCR of IFN$\gamma$, production of IL-2, or cell proliferation. To enrich for human T cells, the mononuclear cell fraction was obtained by centrifugation of heparinated human blood through Nycoprep-Human (Accurate Chemical). After washing, the cells were stained with monoclonal antibodies (Becton Dickinson) against human IgM, CD19, CD14, CD33, and HLA-DR and then panned on petri dishes coated with anti-mouse IgG to remove B cells, monocytes/macrophages, granulocytes and activated T cells. The unattached cells were harvested and cultured as described above for the mouse cells.

The murine T cell clone CTLL-2 was maintained in complete DMEM+10% FBS supplemented with 30 ng/ml of recombinant human IL-2. To remove IL-2, growing cells (less than $10^6$ cells/ml) were harvested by centrifugation and washed 3 times in cold PBS +3% FBS. They were then resuspended in the media without IL-2 at $10^6$ cells/ml and cultured.

COS-7 cells were transfected using the calcium phosphate precipitation method as described (Graham and van de Eb, 1973; Turner et al 1990). And the cells were harvested 60 hours after the addition of DNA for further studies.

CTLL-2 cells were transfected by the following procedure: $10^7$ growing cells were spun down by centrifugaton and resuspended in media without IL-2. 30 ngs of the plasmid DNA were added to the cells and the mixture was electroporated in 0.4 mm cuvette at 1.2 KV and 25mF (BioRad). The cells were allowed to recover overnight in normal CTLL-2 growth media. Those cells that did not survive were removed by spinning through Nycoprep (Accurate Chemical) and the rest were cultured in media containing 1 mg/ml G418 (Boehringer Mannheim). A healthy culture of the stable transfectants was normally obtained in 2–3 weeks.

Differential cDNA Display and Cloning of DPK

Total RNA was prepared from primary mouse T cells cultured with or without PMA/ionomycin stimulation using the RNEasy kit from Qiagen. Contaminating DNA was removed by treatment with RNase-free DNase I (Boehringer Mannheim) for 2–3 hours at 37° C. After repurification using the RNeasy column, the RNA was subjected to differential cDNA display analyses using different combination of 4 anchoring primers and random primers (GeneHunter). The experimental conditions were as recommended by the supplier.

The initial mouse DPK CDNA fragment obtained from differential cDNA display was further extended by Marathion RACE (Clonetech). And the 5'RACE product was used as the probe to screen a mouse thymus cDNA library in the lZAP vector using components from Stratagene. The sequence of the full-length cDNA was assembled from the cDNA clones and several PCR fragments. To clone the human homolog, a PCR fragment was amplified from human brain cDNA using primers derived from the mouse DPK coding region and used as the probe to screen a human fetal brain cDNA library (Statagene).

Tagging the human DPK with the HA epitope at the C-terminal domain was achieved by PCR-mediated mutagenesis. A small fragment (less than 500 bps) encompassing the tagged region was cloned, sequenced and finally swapped back to the full length cDNA via standard molecular biology techniques. The HA-tagged cDNA was put into pBluescript (Stratagene) for in vitro transcription/ translation. The construct was cloned into pSM (Brodsky et al, 1990) or PMV7 (Kirschmeier et al, 1988) vector for transfection into COS-7 and CTLL-2 cells, respectively.

Cell Survival and Apoptosis Assays

Stably transfected CTLL-2 cells were maintained in selective media as described above. At various time points after IL-2 withdrawal, an aliquot of each culture was taken and then mixed with equal volume of Trypan Blue Stain (Life Technologies). The density of live cells which excluded the dye was determined using a hemocytometer. The numbers were from 3 triplicate cultures for each cell line; and are normalized against the average at time 0 for easy comparison between the different cell lines.

To directly study apoptosis, CTLL-2 derived cells were starved for IL-2 overnight (14–16 hrs) and then stained with FITC-conjugated Annexin-V (Pharmingen). After the addition of 0.2 mg/ml propidium iodide, cell surface fluorescence was analyzed on a FACScan machine (Becton Dickinson).

Interactions of DPK and Cyclins In Vitro

These were carried out essentially as described (Tassan et al, 1995). Briefly, 35S-labeled DPK and various cyclins were produced using the TNT systems from Promega under manufacturer suggested conditions. Then DPK was added to each cyclin in separate tubes. After incubating at 4° C. for 2 hours, DPK was isolated by immunoprecipitation with the anti-HA monoclonal antibody (BabCo). The proteins were then separated on SDS/PAGE and visualized by autoradiography. For positive control, we demonstrated the association of CDK2 with cyclin-A under identical conditions (except that polyclonal antibodies against CDK2 were used for immunoprecipitation).

GST and GST-cyclin-C fusion were produced from pGEX-KG and purified from E.coli as described (Smith and Johnson, 1988). Approximately 2 ugs of the protein were mixed with 10 ml of GSH-agarose beads plus either 35S-labeled DPK or total lysates of transfected COS-7 cells. After rocking for 2 hours at 4° C., the beads were harvested and washed 10 times in cold wash buffer (PBS+1% Triton X-100). DPK protein bound to the beads were detected by SDS/PAGE followed by autoradiography or immunoblot using anti-HA antibody.

Immunological Methods

Preparation of total cell lysates, immunoprecipitation, and immunoblot were carried out essentially as described (Xu and Littman, 1993). Immunoblots were developed with the Super Signal substrates from Pierce.

As described, for immunofluorescence microscopy, transiently transfected COS-7 cells were first fixed in 4% paraformaldehyde solution for 5 minutes at room temperature (Chen et al, 1996). After permeabilization with PBS+0.2 % Triton X-100 for 3 minutes, the cells were subjected to indirect immunofluorescence staining using anti-HA monoclonal antibody (1:1000 dilution) and FITC-conjugated donkey anti-mouse IgG (1:100 dilution; Jackson ImmunoResearch Laboratories). Subsequently, they were examined under a fluorescence microscope.

Example 1

Identification of a Gene Induced in T Cells Undergoing Apoptosis

Primary T cells are prone to apoptosis when cultured in the absence of activating stimuli. To identify additional genes in the cell death pathway, we isolated T cells from mouse peripheral lymph nodes and analyzed the gene expression pattern by differential cDNA display (Liang an d Pardee, 1992; Liang et al, 1993). As shown in FIG. 1a, one of the primer sets tested gave rise to a PCR (polymerase-chain-reaction) band that was much more pronounced in the unstimulated, dying T cells than in the activated, proliferating cells. This DNA fragment was cloned and the nucleotide sequence determined. Based on the information obtained, we subsequently isolated corresponding cDNA clones from a mouse thymus cDNA library. The differential expression of the mRNA was confirmed by Northern hybridization using a full-length cDNA clone as the probe (FIG. 1b). The mouse mRNA has two forms of approximately 4 kb and 6 kb in length respectively, due to the alternative polyadenylation at the 3'-untranslated region (data not shown). Both forms are regulated in a similar fashion in T cells.

To obtain the humaoligonucleot oligonucleotides derived from the coding region of the mouse cDNA were used as primers to amplify the human cDNA and the resulting PCR fragment was used as the probe to screen a human fetal brain cDNA library. The sequence of a complete cDNA clone is shown in FIG. 2a. The encoded protein consists of 502 amino acids and contains all the conserved features of a serine/threonine kinase (Hanks et al, 1988). The protein also contains the SACRE (SEQ ID NO:6) motif at a region corresponding to the PSTAIE (SEQ ID NO:7) cyclin-binding domain of CDC2 kinase (Meyerson et al, 1992; Tassan et al, 1995). We named this exemplary gene DPK-1 (death-preventing kinase number 1) based on its induction in apoptotic cells and its structural features. A search of the Genbank database revealed that DPK-1 is most closely related to CDK8 with an 88% homology at the amino acid level (FIG. 2c) and 74% identity at the nucleotide level in the coding region. Interestingly, the proteins are quite divergent near the C-terminus with two regions missing in CDK8. DPK appears to be highly conserved in evolution. The deduced amino acid sequence of mouse and human DPK-1 are nearly 96% identical (FIG. 2b) and genomic DNA from all the species tested (i.e., mouse, hamster, rat, rabbit, pig, dog, cat, cow, sheep, marmoset, and human) hybridized with the mouse CDNA probe under fairly stringent conditions (data not shown). These results suggest that DPK may serve an important biological function in various animal species.

Example 2

Expression of the DPK Gene

As a step toward understanding its biological roles, we analyzed the expression of human DPK gene in the peripheral blood T lymphocytes by reverse transcription coupled PCR (RT-PCR). The results are shown in FIG. 4. Similar to the mouse cells, T cells that had been activated to proliferate expressed a very low level of DPK (lane 1, top panel). On the other hand, those cells that were cultured without stimuli had a high level of DPK message (lane 2, top panel). Significantly, very little DPK mRNA was detected in freshly isolated resting T cells that were not actively dividing (lane 3, top panel). The data indicates that increased expression of DPK was not due to the exit of cell cycle per se but was specific for cells subjected to apoptosis induction. In sharp contrast to DPK, the CDK8 message was much more abundant in dividing cells than in nondividing or apoptotic T cells. These results suggests that the function of these two closely related kinases may be quite distinct.

Figure 5:
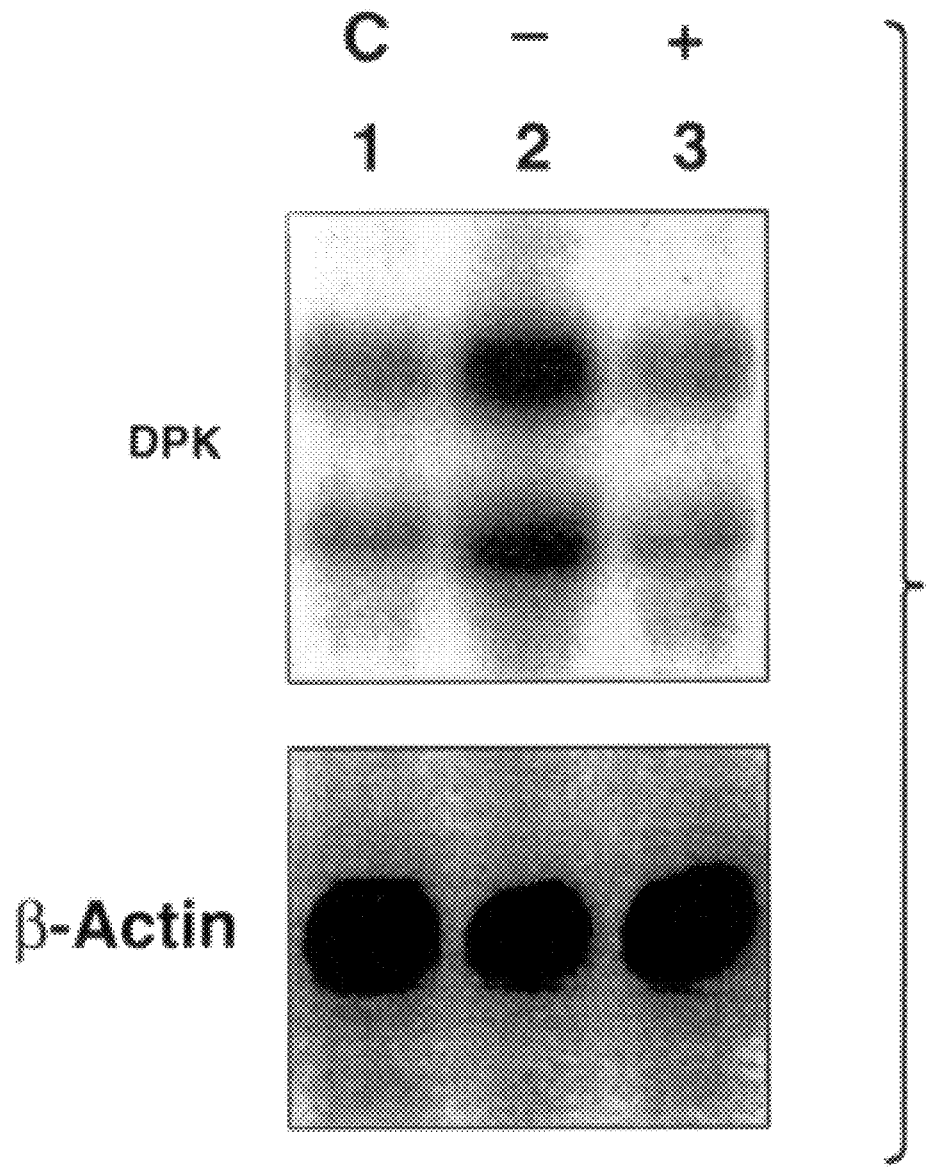
FIG. 5 depicts the regulation of DPK expression in IL-2-dependent murine T cell clone CTLL-2. Total RNA was prepared from control cells grown in media containing IL-2 (lane "C"); cells cultured overnight in the absence of IL-2 (lane "−"); and cells restimulated with IL-2 for 5 hours after overnight starvation (lane "+"). Northern hybridization analyses were then performed using the indicated probes.

Additionally, we studied DPK expression in the murine CTLL-2 T cell clone which is dependent upon IL-2 for growth. Northern hybridization experiments indicated that DPK is similarly regulated in these cells as in the primary T cells (FIG. 5). The induction of DPK expression upon IL-2 withdrawal ranged from 3–9 fold in different experiments, depending on the basal level which appeared to correlate well with the health of the cultures. Time course study indicated that DPK induction was a relatively late event after growth factor deprivation, around the same time (12 hrs) that the cells began to show morphological changes. The elevated DPK expression persisted until most cells (generally more than 80% by 24 hours) had died. The induction of DPK expression was reversed when IL-2 was added back to the culture, indicating that those cells expressing DPK were probably not committed to apoptosis yet. Similar regulation of DPK was also observed in another factor dependent cell line (murine 32D cells of the myeloid lineage) although the level of induction was not as dramatic probably due to the higher basal level of DPK mRNA in these cells (data not shown).

DPK appears to be widely but unevenly expressed in various tissues. Northern hybridization analyses revealed that DPK is expressed at a high level in human brain, heart, and placenta; in mouse, the DPK mRNA is most abundant in the brain, thymus and bone marrow (data not shown).

Example 3

Association of DPK with Cyclin C and its Intracellular Localization

Figures 6A, 6B:
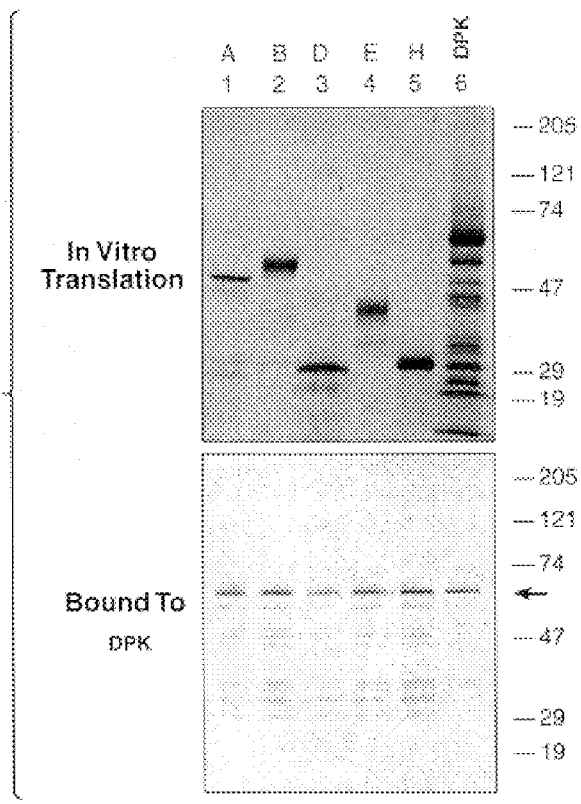
FIGS. 6a and b show that there is no interaction between DPK and cyclins A, B, D, E, and H (6a). The proteins were produced by in vitro transcription/ translation in the presence of 35S-methionine and a fraction of each was separated by SDS/PAGE and detected by autoradiography (upper panel). DPK was incubated with each cyclin or by itself. Following immunoprecipitation of DPK, the proteins were analyzed by SDS/PAGE and autoradiography (lower panel). No cyclin was detected in DPK precipitates. The arrow points to the full-length DPK protein. As the positive control (6b), cyclin A (lane 1) and CDC2 (lane 2) were shown to form a complex which can be co-immunoprecipitated with anti-CDC2 antibodies under identical conditions (lane 3).

Since DPK shows significant homology to members of the CDK family, especially CDK8, we examined its ability to associate with various cyclins. Epitope-tagged DPK and cyclins A, B, D1, E and H were produced by in vitro transcription and translation. The DPK protein was then incubated with each of the cyclins separately. Association between the cyclin and DPK was assessed by gel electrophoresis and autoradiography following immunoprecipitation of DPK with the anti-tag antibody. None of the above cyclins showed detectable association with DPK (FIG. 6).

Figure 7A:
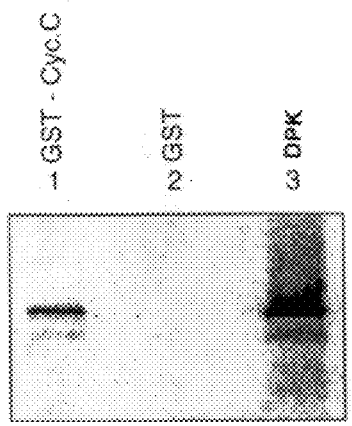
FIGS. 7a–b depict the association of DPK with cyclin C. (7a) Purified GST and GST-cyclin C proteins were incubated with 35S-labeled DPK produced in vitro. Proteins associated with GST or GST-cyclin C were precipitated with GSH-Agarose beads. Following SDS/PAGE, DPK was detected by autoradiography. As the marker, a fraction of the 35S-labeled DPK protein was separated on the same gel (lane 3). (7b) GST-cyclin C or GST protein was incubated with total lysate of COS-7 cells transiently expressing human DPK, and then precipitated with GSH-Agarose beads (lanes 1 and 2). DPK was detected by immunoblot following SDS/PAGE. Total lysates of COS-7 cells transfected with DPK or the vector alone were included in the blots as controls (lane 3 and 4).
Figure 7B:
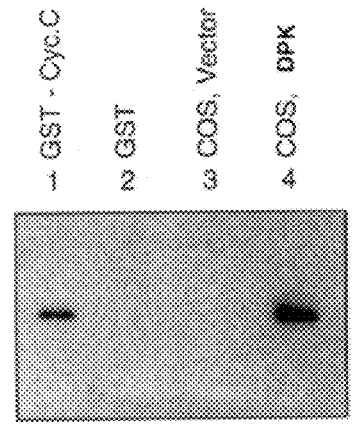

To test the possible interaction of DPK with cyclin C, we introduced a GST-cyclin C fusion construct into *E. coli* and isolated the protein via affinity purification using glutathione (GSH) Sepharose beads. When incubated with the GST-cyclin C fusion protein, the in vitro generated, 35S-labeled DPK protein was found to bind to the GSH beads, indicating an association between the two proteins (FIG. 7a). This interaction can also be demonstrated in another way. We transiently transfected the epitope-tagged DPK into COS cells and prepared total cell extract. The lysate was then incubated with the GST-cyclin C fusion protein. After precipitation with the GSH beads, the bound proteins were separated by SDS/PAGE and transferred to membrane. Western blot was carried out using monoclonal antibody against the epitope-tag and the results clearly showed an association between DPK and cyclin C (FIG. 7b).

Next, we determined the intracellular localization of DPK by immunofluorescent microscopy. COS cells were transiently transfected with an expression construct of the epitope-tagged DPK and fixed. They were then stained with the anti-tag antibody followed by fluorescently labeled secondary antibody. The fluorescent signal was localized to the nucleus (data not shown). It has been proposed that mammalian cyclin C, like the related yeast cyclin SRB 11, plays a role in transcriptional regulation together with its kinase partner (Tassan et al, 1995). Our results are consistent with this proposal.

Example 4

Effects of DPK Expression on Growth Factor Deprivation Induced Cell Death

Figure 8A:
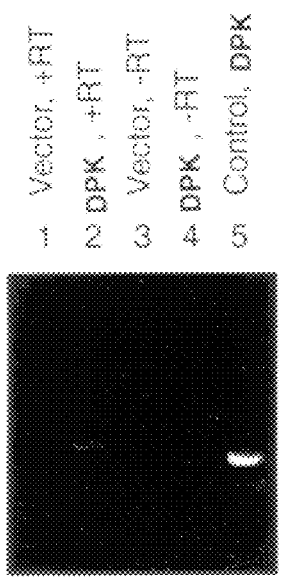
FIGS. 8a–c depicts delayed onset of apoptosis in IL-2 dependent mouse T cells constitutively expressing DPK. CTLL-2 cells were stably transfected with human DPK expression construct or the vector alone. The expression of human DPK mRNA was confirmed by RT-PCR (8a), lane 2; and no reverse transcriptase reactions and cloned human DPK cDNA were included as negative and positive controls, respectively (lanes 3–5). Cell survival (8b) after IL-2 withdrawal was determined by Trypan-blue staining. The numbers shown are the average of triplicate cultures and are normalized against the average at time 0 (100%) for each cell line. Standard deviations are included in the graphs. For apoptosis assays (8c), cells cultured in the presence or absence of IL-2 overnight were stained with FITC-Annexin-V and PI followed by FACS analyses. Dying cells are PI−Annexin+ and dead cells are PI+Annexin±. The number in each quadrant indicates the percentage of that cell population.
Figure 8B:
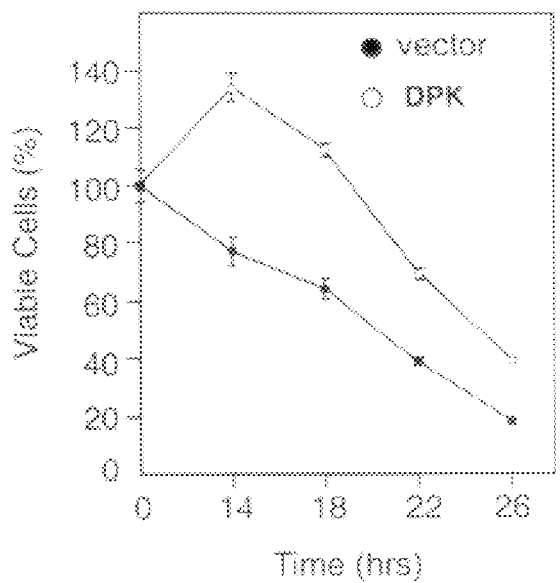
Figure 8D:
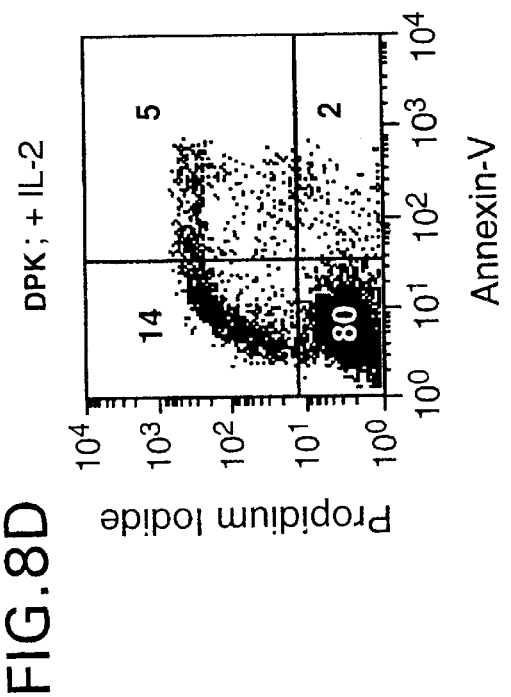
Figure 8F:
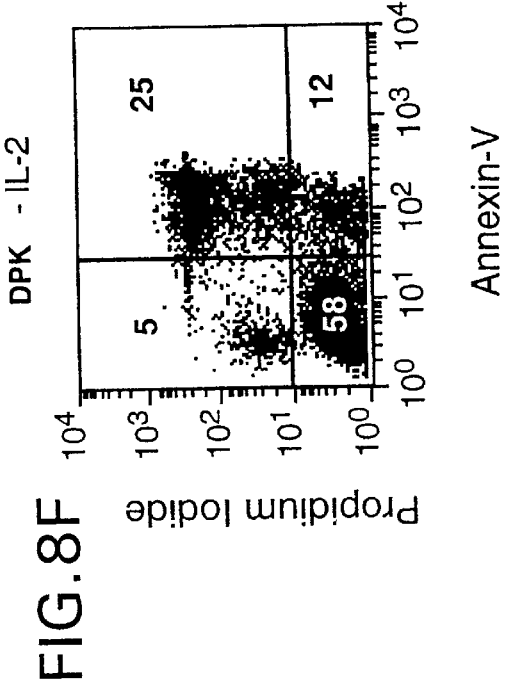
Figure 8C:
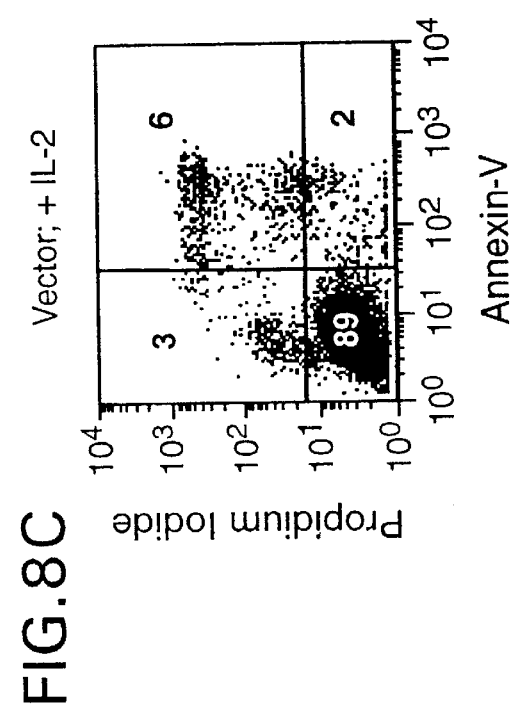
Figure 8E:
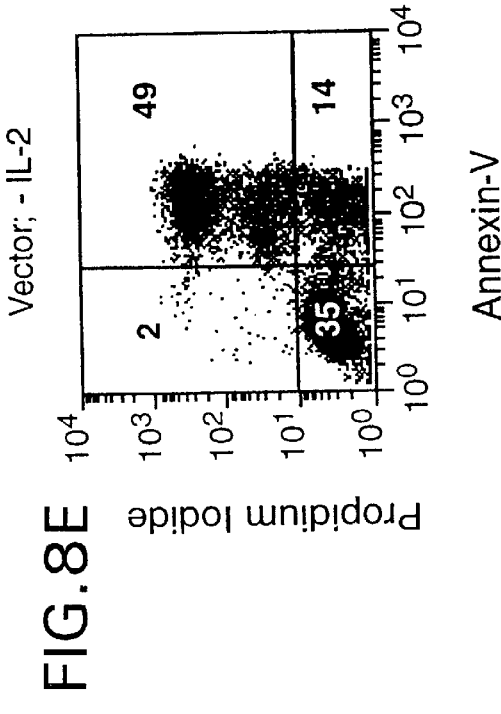

Elevated expression of DPK in cells induced for apoptosis suggests that it may play a role (either positive or negative) in the regulation of cell death. The murine T cell clone CTLL-2 appears to be an ideal model system for testing this possibility: first, apoptosis can be readily induced by removing IL-2 from the media; secondly, DPK transcription is regulated in the same manner as in primary T cells. Thus we stably transfected CTLL-2 cells with an expression construct where human DPK cDNA was put under the control of MMLV LTR, a constitutive promoter. The expression of the human message was confirmed by RT-PCR using human-specific primers (FIG. 8a). When starved for IL-2, cells expressing human DPK showed increased survival at various time points compared to the negative control cells transfected with the vector alone (FIG. 8b). In fact, we could still find a few live cells in the population transfected with the DPK construct long after the control cells have completely died (data not shown). In addition to viability assays, we also studied cell death directly. It has been reported that cells start to lose the membrane asymmetry at the early stage of apoptosis. As a result, phosphatidylserine becomes exposed on the cell surface and can be detected by its binding to Annexin-V, a calcium-dependent phospholipid-binding protein (Vermes et al, 1995). Propidium iodide (PI) is a vital dye that only stains dead cells. Therefore, FACS analysis following double staining with annexin-V and PI can be used to determine the degree of apoptosis in a given population of cells. When the CTLL-2 derived cells were analyzed in this fashion, the data indicated that there was a significant decrease in the percentage of dead and dying cells after IL-2 withdrawal when DPK was ectopically expressed (FIG. 8c). Thus it appears that the normal function of DPK is to suppress cell death (at least temporarily) under unfavorable physiological conditions.

Figure 9C:
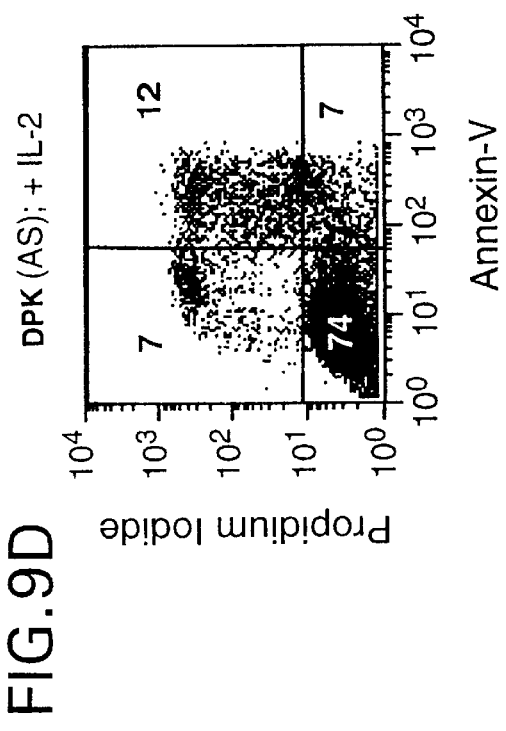
FIGS. 9a–c shows accelerated cell death following growth factor withdrawal in cells expressing antisense DPK mRNA. CTLL-2 cells were stably transfected with mouse DPK antisense expression construct or the vector alone. Antisense DPK expression was verified by RNase protection assay using the sense probe (9a). Cell survival (9b) and apoptosis (9c) were analyzed as described in FIG. 9.
Figure 9E:
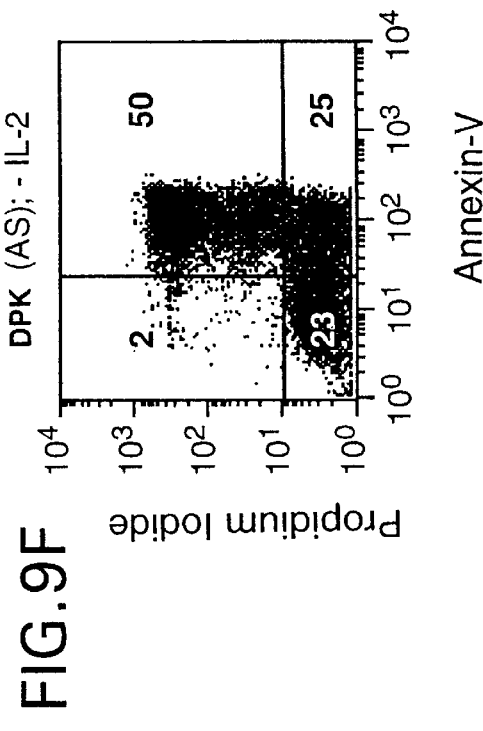
Figure 9D:
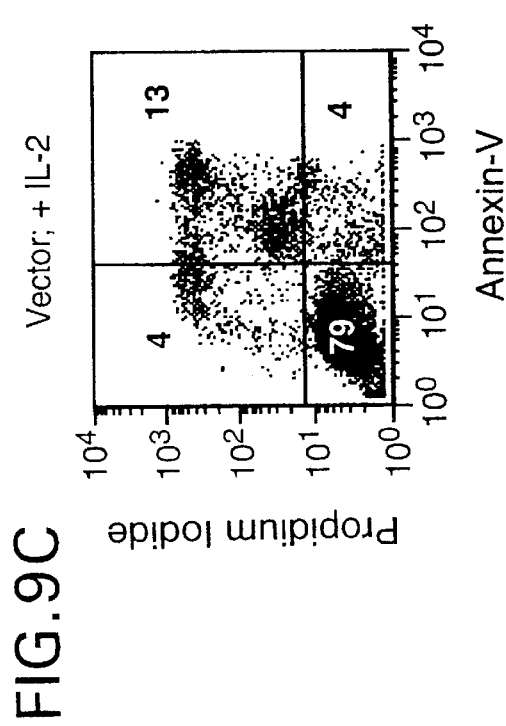
Figure 9F:
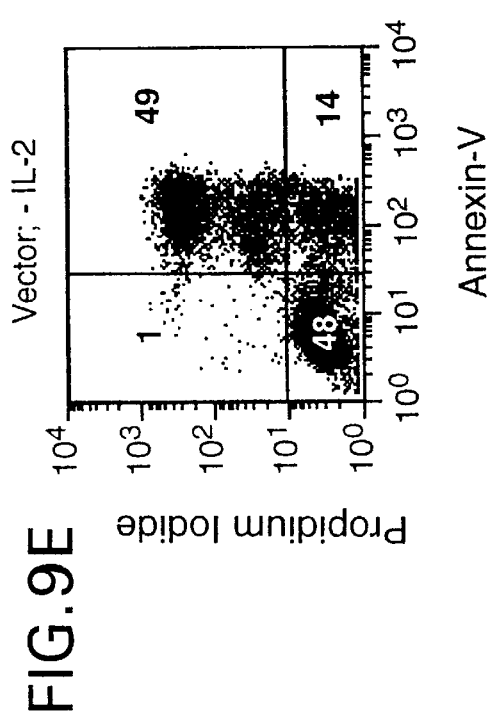

Based on the above observations, we reasoned that disrupting the expression of the endogenous DPK gene should lead to accelerated cell death. A construct which expresses the mouse DPK cDNA in the antisense orientation was introduced into CTLL-2 cells by electroporation. Cells stably harbor the expression vector were expanded in the appropriate selective media. Compared to the control cells transfected with the empty vector, these cells grow at a fairly normal rate although the culture appears to contain slightly more dead cells in general (data not shown). Ribonuclease protection assay using the sense probe demonstrated the presence of the antisense message in the cells (FIG. 9a). When subjected to IL-2 starvation, cells expressing the antisense DPK were clearly more susceptible to apoptosis and had lower viability compared to the control population (FIG. 9b,c). These results further support an anti-apoptosis function for DPK.

Discussion

Our search for additional players in the pathway of programmed cell death led to the isolation of DPK-1, a novel serine/threonine kinase of the CDK family. The gene is highly conserved in evolution. Furthermore, the regulation and function of DPK proteins appear nearly identical in mouse and human T cells. The expression of DPK is strongly induced in T cells (and likely other cell types as well) by apoptotic signals such as the lack of a growth factor. DPK may act as a negative regulator of cell death since its constitutive expression from an heterologous promoter leads to prolonged cell survival after growth factor withdrawal. This is further supported by the fact that cell death was significantly accelerated when endogenous DPK production was disturbed by expressing the antisense message. We also showed that the DPK protein is specifically associated with cyclin C in vitro and is localized to the nucleus.

Although DPK and CDK8 share the same cyclin C partner and are highly homologous to each other, the two kinases are apparently regulated in very different manners. DPK is preferentially expressed in cells stimulated by a death signal, whereas the highest level of CDK8 message is found in actively dividing cells. The distinct expression pattern of these two genes suggests they may have unique functions in the cell. CDK8 was originally cloned based on its sequence homology to CDK family of kinases and its biological function is unknown at present (Tassan et al, 1995).

As described in the previous section, constitutively expressed DPK has a significant but not dramatic effect on T cell apoptosis induced by growth factor starvation. This is probably caused by a low level of DPK expression in these cells. In the case of the sense expression construct, the mRNA was barely visible on Northern hybridization blot and we failed to detect the protein by immunoblot blot analysis using the anti-tag antibody (data not shown). As for the antisense message, its level is approximately the same as that of endogenous DPK mRNA in healthy, proliferating cells and thus at least several fold less than the peak level of the endogenous message induced by growth factor deprivation (data not shown). Although the MMLV LTR promoter we used usually gave adequate expression in the murine T cells, it has been reported that the retroviral promoter may be down-regulated gradually once introduced into cells (Kitamura et al, 1995). The cells we studied have been maintained in the selective media for a relatively long time in order to obtain stable transfectants. In fact, we did observed a decrease in the expression level with time (data not shown). However, based on the fact that viable CTLL-2 cells containing the human DPK expression construct could still be recovered several days after IL-2 withdrawal when all the control cells had died, it appears that DPK at a high level has a pronounced effect on cell death.

REFERENCES

Askew, D. S., Ashmun, R. A., Simmons, B. C., and Cleveland, J. L. 1991. Constitutive c-myc expression in an IL-3-dependent myeloid cell line supresses cell cycle arrest and accelerates apoptosis. Oncogene 6: 1915–1922.

Beg, A. A., and Baldwin, A. S. 1996. An essential role for NF-kB in preventing TNFa-induced cell death. Science 274: 782–784.

Boise, L. H., Gonzalez-Garcia, M., Postema, C. E., Ding, L., Lindsten,T., Turka, L. A., Mao, X., Nunez, G., and Thompson, C. B. 1993. Bcl-x, a bcl-2-related gene that functions as a dominant regulator of apoptotic cell death. Cell 74: 597–608.

Brodsky, M. H., Wharton, M., Myers, R. M., and Littman, D. R. 1990. Analysis of the site in CD4 that binds to the HIV envelope glycoprotein. J. Immunol. 144: 3878–3886.

Carson, D. A. 1995. Cancer progression and p53. Lancet 346: 1009–1011.

Chen, C. -M. A., Krout, N., Groudine, M., and Weintraub, H. 1996. I-mf, a novel myogenic repressor, interacts with members of the MyoD family. Cell 86: 731–741.

Evan, G. I., Wyllie, A. H., Gilbert, C. S., Littlewood, T. D., Land, H., Brooks, M., Waters, C. M., Penn, L. Z., and Hancock, D. C. 1992. Induction of apoptosis in fibroblasts by c-myc protein. Cell 69: 119–128.

Feaver, W. J., Svejstrup, J. Q., Henry, N. L., and Kornberg, R. D. 1994. Relationship of CDK-activating kinase and RNA polymerase II CTD kinase TFIIH/TFIIK. Cell 79: 1103–1109.

Graham, F. L., and van der Eb, J. 1973. A new technique for the assay of infectivity of human adenovirus 5 DNA. Virology 52: 456–467.

Hanks, S. K., Quinn, A. M., and Hunter, T. 1988. The protein kinase family: conserved features and deduced phylogeny of the catalytic domains. Science 241: 42–52.

Hellmich, M. R., Pant, H. C., Wada, E., and Battey, J. F. 1992. Neuronal cdc2-like kinase: a cdc2-related kinase with predominantly neuronal expression. Proc. Natl. Acad. Sci. USA 89: 10867–10871.

Hengartner, M. O., and Horvitz, H. R. 1994. C. elegans cell survival gene ced-9 encodes a functional homolog of the mammalian proto-oncogene bcl-2. Cell 76: 665–676.

Henkart, P. A. 1996. ICE family proteases:mediators of all apoptotic cell death? Immunity 4: 195–201.

Hirst, K., Fisher, F., McAndrew, P. C., and Goding, C. R. 1994. The transcription factor, the Cdk, its cyclin and their regulator: directing the transcriptional response to a nutritional signal. EMBO J. 13: 5410–5420.

Hsu, H., Xiong, J., and Goeddel, D. V. 1995. The TNF receptor-l-associated protein TRADD signals cell death and NF-kB activation. Cell 81: 495–504.

Jacobson, M. D. 1997. Apoptosis: Bcl-2-related proteins get connected. Curr. Biol. 7: R277-281.

Kirschmeier, P. T., Housey, G. M., Johnson, M. D., Perkins, A. S., and Weinstein, I. B. 1988. DNA 7: 219–225.

Kitamura, T., Onishi, M., Kinoshita, S., Shibuya, A., Miyajima, A., and Nolan G. P. 1995. Efficient screening of retroviral cDNA expression libraries.

Kolodziej, P. A., and Young, R. A. 1991. Epitope tagging and protein surveillance. Meth. Enz. 194: 508–519.

Kluck, R. M., Bossy-Weitzel, E., Green, D. R., and Newmeyer, D. D. 1997. The release of cytochrome c from mitochondria: a primary site for Bcl-2 regulation of apoptosis. Science 275: 1132–1136.

Leclerc, V., Tassan, J. -P., O'Farrell, P. H., Nigg, E. A., and Leopold, P. 1996. Mol. Biol. Cell 7: 505–513.

Liang, P., and Pardee, A. B. 1992. Differential display of eukaryotic messenger RNA by means of the polymerase chain reaction. Science 257: 967–970.

Liang, P., Averboukh, l., and Pardee, A. B. 1993. Distribution and cloning of eukaryotic mRNAs by means of differential display: refinements and optimization. Nuc. Acids Res. 21: 3269–3275.

Liao, S., Zhang, J., Jeffery, D. A., Koleske, A. J., Thompson, C. M., Chao, D. M., Viljoen, M., van Vuuren, H. J. J., and Young, R. A. 1995. A kinase-cyclin pair in the RNA polymerase II holoenzyme. Nature 374: 193–196.

Meyerson, M., Enders, G. H., Wu, C. -L., Su, L. -K., Gorka, C., Nelson, C., Harlow, E., and Tsai, L. -H. 1992. A family of human cdc2-related protein kinases. EMBO J. 11: 2909–2917.

Minn, A. J., Velez, P., Schendel, S. L., Liang, H., Muchmore, S. W., Fesik, S. W., Fill, M., and Thompson, C. B. 1997. Bcl-x(L) forms an ion channel in synthetic lipid membranes. Nature 385: 353–357.

Miura, M., and Yuan, J. 1996. Mechanisms of programmed cell death in Caenorhabditis elegans and vertebrates. Curr. Topics. Dev. Biol. 32: 139–174.

Morgan, D. 0. 1995. Principles of CDK regulation. Nature 374: 131–134.

Oltvai, Z. N., Milliman, C. L., and Korsmeyer, S. J. 1993. Bcl-2 heterodimerizes in vivo with a conserved homolog, Bax, that accelerates programmed cell death. Cell 74: 609–619.

Reed, J. C. 1997. Double identity for proteins of the Bcl-2 family. Nature 387: 773–776.

Roy, R., Adamczewski, J. P., Seroz, T., Vermeulen, W., Tassan, J. P., Schaeffer, L., Nigg, E. A., Hoeijmakers, J. H., and Egly, J. M. 1994. The MO15 cell cycle kinase is associated with the TFIIH transcription-DNA repair factor. Cell 79: 1093–1101.

Rudin, C. M., and Thompson, C. B. 1997. Apoptosis and disease: regulation and clinical relevance of programmed cell death. Ann. Rev. Med. 48: 267–81.

Serizawa, H., Makela, T. P., Conaway, J. W., Conaway, R. C., Weinberg, R. A., and Young, R. A. 1995. Association of Cdk-activating kinase subunits with transcription factor TFIIH. Nature 374: 280–282.

Shetty, K. T., Link, W. T., and Pant, H. C. 1993. cdc2-like kinase from rat spinal cord specifically phosphorylates KSPXK motifs in neurofilament proteins: isolation and characterization. Proc. Natl. Acad. Sci. 90: 6844–6848.

Shiekhattar, R., Mermelstein, F., Fisher, R. P., Drapkin, R., Dynlacht, B., Wessling, H. C., Morgan, D. O., and Reinberg, D. 1995. Cdk-activating kinase complex is a component of human transcription factor TFIIH. Nature 374: 283–287.

Smith, D. B., and Johnson, K. S. 1988. Single-step purification of polypeptides expressed in *Escherichia coli* as fusions with glutathione S-transferase. Gene 67: 31–40.

Tassan, J.-P., Jaquenoud, M., Leopold, P., Schultz, S. J., and Nigg, E. A. 1995. Identification of human cyclin-dependent kinase 8, a putative protein kinase partner for cyclin C. Proc. Natl. Acad. Sci. 92: 8871–8875.

Turner, J. M., Brodsky, M. H., Irving, B. A., Levin, S. D., Perlmutter, R. M., and Littman, D. R. 1990. Interaction of the unique N-terminal region of tyrosine kinase p56lck with cytoplasmic domains of CD4 and CD8 is mediated by cysteine motifs. Cell 60: 755–765.

Vaux, D. L., Cory, S., and Adams, J. M. 1988. Bcl-2 gene promotes haemopoietic cell survival and cooperates with c-myc to immortalize pre-B cells. Nature 335: 440–442.

Vaux, D. L., Weissman, I. L., and Kim, S. K. 1992. Prevention of programmed cell death in Caenorhabditis elegans by human bcl-2. Science 258: 1955–1957.

Vaux, D.L. and Strasser, A. 1996. The molecular biology of apoptosis. Proc. Natl. Acad. Sci. USA 93: 2239–2244.

Vaux, D. L. 1997. CED-4: the third horseman of apoptosis. Cell 90: 389–390.

Wang, C-Y., Mayo, M. W., and Baldwin, A. S. 1996. TNF- and cancer therapy-induced apoptosis potentiation by inhibition of NF-kB. Science 274: 784–787.

Xu, H., and Littman, D. L. 1993. A kinase-independent function of Lck in potentiating antigen-specific T cell activation. Cell 74: 633–643.

Yang, J., Liu, X., Bhalla, K., Kim, C. N., Ibrado, A. M., Cai, J., Peng, T. I., Jones, D. P., Wang, X. 1997. Prevention of apoptosis by Bcl-2: release of cytochrome c from mitochondria blocked.

Zou, H., Henzel, W. J., Liu, X., Lutzchg, A., and Wang, X. 1997. Apaf-1, a human protein homologous to C. elegans CED-4, participates in cytochrome c-dependent activation of capsase-3. Cell 90: 405–413.

Deposit of DNA

*E. coli* cells containing the vector hu-DPK encoding human cDNA for DPK-1 have been deposited with the ATCC (American Type Culture Collection, 12301 Parklawn Drive, Rockville, MD., USA) on Nov. 4, 1997 and assigned accession number ATCC 98577.

What is claimed is:

1. A Death Preventing Kinase (DPK) polypeptide selected from the group consisying of:
   (a) the polypeptide of SEQ ID NO:2;
   (b) the polypeptide of SEQ ID NO:4;
   (c) a polypeptide encoded by the complement of a nucleic acid molecule that remaims hybridized under washing conditions of 0.2×SSC and 0.1 percent SDS at 50–65° C. to the nucleic acid molecules of SEQ ID NOS:1 or 3, wherein such polypeptide has a biological activity of prolonging the survival of cells similar or identical to (a) or (b); and
   (d) fragments of any of the polypeptides of (a)–(c) above, wherein such fragments have a biological activity of prolonging the survival of cells similar or identical to (a) or (b).

2. A DPK polypeptide according to claim 1 that is the polypeptide of SEQ ID NO:2 or a fragment thereof, wherein said fragment has a biological activity of prolonging the survival of cells similar or identical to (a) or (b).

3. A DPK polypeptide according to claim 1 that is the polypeptide of SEQ ID NO:4 or a fragment thereof, wherein said fragment has a biological activity of prolonging the survival of cells similar or identical to (a) or (b).

4. The DPK polypeptide of any of claims 1, 2 or 3 that does not possess an amino terminal methionine.

* * * * *

UNITED STATES PATENT AND TRADEMARK OFFICE
CERTIFICATE OF CORRECTION

PATENT NO. : 5,981,248

DATED : November 9, 1999

INVENTOR(S) : Hua Xu

It is certified that error appears in the above-identified patent and that said Letters Patent is hereby corrected as shown below:

Column 8, line 13: Change "630C." to -- 63°C. --.

Column 8, line 40: Change "CDNA" to -- cDNA --.

Column 11, line 11: Delete "the".

Column 12, line 32: Change "DHI10" to -- DH10 --.

Column 21, line 4: Change "(Statagene)" to -- (Stratagene) --.

Column 22, line 24: Change "humaoligonucleot" to -- human homologue, --.

Column 45, line 37: Change "consisying" to -- consisting --.

Signed and Sealed this

First Day of August, 2000

*Attest:*

Q. TODD DICKINSON

*Attesting Officer*   *Director of Patents and Trademarks*

SEQUENCE LISTING

```
<160> NUMBER OF SEQ ID NOS: 7

<210> SEQ ID NO 1
<211> LENGTH: 1997
<212> TYPE: DNA
<213> ORGANISM: human
<220> FEATURE:
<221> NAME/KEY: CDS
<222> LOCATION: (181)..(1686)

<400> SEQUENCE: 1
tgtggccgcc gaggagtccc ttgctgaagg cggaccgcgg agcggcgggc ggcgggcggc      60
gcgcgcgcgc gcgcgagagg cggctgttgg agaagtggag cggcggtcgc gggggggagga    120 ggaggaggga ctgagcggcg gcggcccccg cgtcccgtgc ctctatgggg gaagcagaca     180 atg gat tat gat ttc aag gcg aag ctg gcg gcg gag cgg gag cgg gtg       228
Met Asp Tyr Asp Phe Lys Ala Lys Leu Ala Ala Glu Arg Glu Arg Val
  1               5                  10                  15 gag gat ttg ttt gag tac gaa ggg tgc aaa gtg gga cgc ggc acc tac       276
Glu Asp Leu Phe Glu Tyr Glu Gly Cys Lys Val Gly Arg Gly Thr Tyr
             20                  25                  30 ggt cac gtc tac aag gcg agg cgg aaa gat gga aaa gat gaa aag gaa       324
Gly His Val Tyr Lys Ala Arg Arg Lys Asp Gly Lys Asp Glu Lys Glu
         35                  40                  45
```

| | | |
|---|---|---|
| tat gca ttg aag caa att gaa ggc aca gga ata tcc atg tcg gct tgt<br>Tyr Ala Leu Lys Gln Ile Glu Gly Thr Gly Ile Ser Met Ser Ala Cys<br>50 55 60 | | 372 |
| aga gag att gca ctt ttg cga gaa ttg aag cac cct aat gtg att gca<br>Arg Glu Ile Ala Leu Leu Arg Glu Leu Lys His Pro Asn Val Ile Ala<br>65 70 75 80 | | 420 |
| ttg cag aag gtg ttc ctt tct cac agt gac agg aag gta tgg ctg ctg<br>Leu Gln Lys Val Phe Leu Ser His Ser Asp Arg Lys Val Trp Leu Leu<br>85 90 95 | | 468 |
| ttt gat tat gca gag cat gac ttg tgg cat att att aag ttt cac cgt<br>Phe Asp Tyr Ala Glu His Asp Leu Trp His Ile Ile Lys Phe His Arg<br>100 105 110 | | 516 |
| gca tca aaa gca aat aaa aag ccc atg cag ttg cca aga tct atg gtt<br>Ala Ser Lys Ala Asn Lys Lys Pro Met Gln Leu Pro Arg Ser Met Val<br>115 120 125 | | 564 |
| aaa tcc tta ctt tac cag att ctt gat ggt atc cat tac ctc cat gca<br>Lys Ser Leu Leu Tyr Gln Ile Leu Asp Gly Ile His Tyr Leu His Ala<br>130 135 140 | | 612 |
| aat tgg gtg ctt cac aga gac ttg aaa cca gca aat atc cta gta atg<br>Asn Trp Val Leu His Arg Asp Leu Lys Pro Ala Asn Ile Leu Val Met<br>145 150 155 160 | | 660 |
| gga gaa ggt cct gag agg ggg aga gtc aaa ata gct gac atg ggt ttt<br>Gly Glu Gly Pro Glu Arg Gly Arg Val Lys Ile Ala Asp Met Gly Phe<br>165 170 175 | | 708 |
| gcc aga tta ttc aat tct cct cta aag cca cta gca gat ttg gat cca<br>Ala Arg Leu Phe Asn Ser Pro Leu Lys Pro Leu Ala Asp Leu Asp Pro<br>180 185 190 | | 756 |
| gta gtt gtg aca ttt tgg tat cgg gct cca gaa ctt ttg ctt ggt gca<br>Val Val Val Thr Phe Trp Tyr Arg Ala Pro Glu Leu Leu Leu Gly Ala<br>195 200 205 | | 804 |
| agg cat tat aca aag gcc att gat ata tgg gca ata ggt tgt ata ttt<br>Arg His Tyr Thr Lys Ala Ile Asp Ile Trp Ala Ile Gly Cys Ile Phe<br>210 215 220 | | 852 |
| gct gaa ttg ttg act tcg gaa cct att ttt cac tgt cgt cag gaa gat<br>Ala Glu Leu Leu Thr Ser Glu Pro Ile Phe His Cys Arg Gln Glu Asp<br>225 230 235 240 | | 900 |
| ata aaa aca agc aat ccc ttt cat cat gat caa ctg gat cgg ata ttt<br>Ile Lys Thr Ser Asn Pro Phe His His Asp Gln Leu Asp Arg Ile Phe<br>245 250 255 | | 948 |
| agt gtc atg ggg ttt cct gca gat aaa gac tgg gaa gat att aga aag<br>Ser Val Met Gly Phe Pro Ala Asp Lys Asp Trp Glu Asp Ile Arg Lys<br>260 265 270 | | 996 |
| atg cca gaa tat ccc aca ctt caa aaa gac ttt aga aga aca acg tat<br>Met Pro Glu Tyr Pro Thr Leu Gln Lys Asp Phe Arg Arg Thr Thr Tyr<br>275 280 285 | | 1044 |
| gcc aac agt agc ctc ata aag tac atg gag aaa cac aag gtc aag cct<br>Ala Asn Ser Ser Leu Ile Lys Tyr Met Glu Lys His Lys Val Lys Pro<br>290 295 300 | | 1092 |
| gac agc aaa gtg ttc ctc ttg ctt cag aaa ctc ctg acc atg gat cca<br>Asp Ser Lys Val Phe Leu Leu Leu Gln Lys Leu Leu Thr Met Asp Pro<br>305 310 315 320 | | 1140 |
| acc aag aga att acc tcg gag caa gct ctg cag gat ccc tat ttt cag<br>Thr Lys Arg Ile Thr Ser Glu Gln Ala Leu Gln Asp Pro Tyr Phe Gln<br>325 330 335 | | 1188 |
| gag gac cct ttg cca aca tta gat gta ttt gcc ggc tgc cag att cca<br>Glu Asp Pro Leu Pro Thr Leu Asp Val Phe Ala Gly Cys Gln Ile Pro<br>340 345 350 | | 1236 |
| tac ccc aaa cga gaa ttc ctt aat gaa gat gat cct gaa gaa aaa ggt<br>Tyr Pro Lys Arg Glu Phe Leu Asn Glu Asp Asp Pro Glu Glu Lys Gly<br>355 360 365 | | 1284 |

```
gac aag aat cag caa cag cag cag aac cag cat cag cag ccc aca gcc      1332
Asp Lys Asn Gln Gln Gln Gln Gln Asn Gln His Gln Gln Pro Thr Ala
370                 375                 380 cct cca cag cag gca gca gcc cct cca cag gcg ccc cca cca cag cag      1380
Pro Pro Gln Gln Ala Ala Ala Pro Pro Gln Ala Pro Pro Pro Gln Gln
385                 390                 395                 400 aac agc acc cag acc aac ggg acc gca ggt ggg gct ggg gcc ggg gtc      1428
Asn Ser Thr Gln Thr Asn Gly Thr Ala Gly Gly Ala Gly Ala Gly Val
            405                 410                 415 ggg ggc acc gga gca ggg ttg cag cac agc cag gac tcc agc ctg aac      1476
Gly Gly Thr Gly Ala Gly Leu Gln His Ser Gln Asp Ser Ser Leu Asn
        420                 425                 430 cag gtg cct cca aac aag aag cca cgg cta ggg cct tca ggc gca aac      1524
Gln Val Pro Pro Asn Lys Lys Pro Arg Leu Gly Pro Ser Gly Ala Asn
    435                 440                 445 tca ggt gga cct gtg atg ccc tcg gat tat cag cac tcc agt tct cgc      1572
Ser Gly Gly Pro Val Met Pro Ser Asp Tyr Gln His Ser Ser Ser Arg
450                 455                 460 ctg aat tac caa agc agc gtt cag gga tcc tct cag tcc cag agc aca      1620
Leu Asn Tyr Gln Ser Ser Val Gln Gly Ser Ser Gln Ser Gln Ser Thr
465                 470                 475                 480 ctt ggc tac tct tcc tcg tct cag cag agc tca cag tac cac cca tct      1668
Leu Gly Tyr Ser Ser Ser Ser Gln Gln Ser Ser Gln Tyr His Pro Ser
            485                 490                 495 cac cag gcc cac cgg tac tgaccagctc ccgttgggcc aggccagccc              1716
His Gln Ala His Arg Tyr
            500 agcccagagc acaggctcca gcaatatgtc tgcattgaaa agaaccaaaa aaatgcaaac    1776 tatgatgcca tttaaaactc atacacatgg gaggaaaacc ttatatactg agcattgtgc    1836 aggactgata gctcttcttt attgacttaa agaagattct tgtgaagttt ccccagcacc    1896 ccttccctgc atgtgttcca ttgtgacttc tctgataaag cgtctgatct aatcccagca    1956 cttctgtaac cttcagcatt tcttacagcc taagaagaaa g                        1997

<210> SEQ ID NO 2
<211> LENGTH: 502
<212> TYPE: PRT
<213> ORGANISM: human

<400> SEQUENCE: 2

Met Asp Tyr Asp Phe Lys Ala Lys Leu Ala Ala Glu Arg Glu Arg Val
1               5                   10                  15

Glu Asp Leu Phe Glu Tyr Glu Gly Cys Lys Val Gly Arg Gly Thr Tyr
            20                  25                  30

Gly His Val Tyr Lys Ala Arg Arg Lys Asp Gly Lys Asp Glu Lys Glu
        35                  40                  45

Tyr Ala Leu Lys Gln Ile Glu Gly Thr Gly Ile Ser Met Ser Ala Cys
    50                  55                  60

Arg Glu Ile Ala Leu Leu Arg Glu Leu Lys His Pro Asn Val Ile Ala
65                  70                  75                  80

Leu Gln Lys Val Phe Leu Ser His Ser Asp Arg Lys Val Trp Leu Leu
            85                  90                  95

Phe Asp Tyr Ala Glu His Asp Leu Trp His Ile Ile Lys Phe His Arg
        100                 105                 110

Ala Ser Lys Ala Asn Lys Lys Pro Met Gln Leu Pro Arg Ser Met Val
    115                 120                 125

Lys Ser Leu Leu Tyr Gln Ile Leu Asp Gly Ile His Tyr Leu His Ala
130                 135                 140
```

```
Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
            165                 170                 175

Ala Arg Leu Phe Asn Ser Pro Leu Lys Pro Leu Ala Asp Leu Asp Pro
            180                 185                 190

Val Val Val Thr Phe Trp Tyr Arg Ala Pro Glu Leu Leu Leu Gly Ala
            195                 200                 205

Arg His Tyr Thr Lys Ala Ile Asp Ile Trp Ala Ile Gly Cys Ile Phe
210                 215                 220

Ala Glu Leu Leu Thr Ser Glu Pro Ile Phe His Cys Arg Gln Glu Asp
225                 230                 235                 240

Ile Lys Thr Ser Asn Pro Phe His His Asp Gln Leu Asp Arg Ile Phe
                245                 250                 255

Ser Val Met Gly Phe Pro Ala Asp Lys Asp Trp Glu Asp Ile Arg Lys
            260                 265                 270

Met Pro Glu Tyr Pro Thr Leu Gln Lys Asp Phe Arg Arg Thr Thr Tyr
            275                 280                 285

Ala Asn Ser Ser Leu Ile Lys Tyr Met Glu Lys His Lys Val Lys Pro
290                 295                 300

Asp Ser Lys Val Phe Leu Leu Leu Gln Lys Leu Leu Thr Met Asp Pro
305                 310                 315                 320

Thr Lys Arg Ile Thr Ser Glu Gln Ala Leu Gln Asp Pro Tyr Phe Gln
                325                 330                 335

Glu Asp Pro Leu Pro Thr Leu Asp Val Phe Ala Gly Cys Gln Ile Pro
            340                 345                 350

Tyr Pro Lys Arg Glu Phe Leu Asn Glu Asp Pro Glu Glu Lys Gly
            355                 360                 365

Asp Lys Asn Gln Gln Gln Gln Asn Gln His Gln Pro Thr Ala
            370                 375                 380

Pro Pro Gln Gln Ala Ala Ala Pro Pro Gln Ala Pro Pro Gln Gln
385                 390                 395                 400

Asn Ser Thr Gln Thr Asn Gly Thr Ala Gly Ala Gly Ala Gly Val
                405                 410                 415

Gly Gly Thr Gly Ala Gly Leu Gln His Ser Gln Asp Ser Ser Leu Asn
            420                 425                 430

Gln Val Pro Pro Asn Lys Lys Pro Arg Leu Gly Pro Ser Gly Ala Asn
            435                 440                 445

Ser Gly Gly Pro Val Met Pro Ser Asp Tyr Gln His Ser Ser Ser Arg
450                 455                 460

Leu Asn Tyr Gln Ser Ser Val Gln Gly Ser Ser Gln Ser Gln Ser Thr
465                 470                 475                 480

Leu Gly Tyr Ser Ser Ser Ser Gln Gln Ser Ser Gln Tyr His Pro Ser
                485                 490                 495

His Gln Ala His Arg Tyr
            500

<210> SEQ ID NO 3
<211> LENGTH: 3891
<212> TYPE: DNA
<213> ORGANISM: mouse
<220> FEATURE:
<221> NAME/KEY: CDS
<222> LOCATION: (63)..(1565)

<400> SEQUENCE: 3
```

-continued

```
tggaggaggg actgagtggc ggcggccccc gcgtcccggt ttctctatgg gggaagcaga        60 ca atg gat tat gat ttc aag gcg aag ctg gcg gcg gag cgg gag cgg         107
   Met Asp Tyr Asp Phe Lys Ala Lys Leu Ala Ala Glu Arg Glu Arg
   1               5                   10                  15 gtg gag gat ctg ttt gag tac gaa ggg tgc aaa gtg gga cgc ggc acc        155
Val Glu Asp Leu Phe Glu Tyr Glu Gly Cys Lys Val Gly Arg Gly Thr
                20                  25                  30 tac ggg cat gtc tac aag gcg agg cgg aaa gat gga aaa gat gaa aag        203
Tyr Gly His Val Tyr Lys Ala Arg Arg Lys Asp Gly Lys Asp Glu Lys
                35                  40                  45 gaa tat gca ctt aag caa atc gaa ggc aca gga ata tct atg tcg gct        251
Glu Tyr Ala Leu Lys Gln Ile Glu Gly Thr Gly Ile Ser Met Ser Ala
        50                  55                  60 tgt aaa gag att gca ctt ttg aga gaa ctg aac cac cct aat gtg atc        299
Cys Lys Glu Ile Ala Leu Leu Arg Glu Leu Asn His Pro Asn Val Ile
    65                  70                  75 gca ttg caa aag gtg ttc ctt tct cac agc gac agg aag gtg tgg ctg        347
Ala Leu Gln Lys Val Phe Leu Ser His Ser Asp Arg Lys Val Trp Leu
80                  85                  90                  95 ctg ttt gac tat gca aaa cat gac ctt tgg cat att att aat ttt cac        395
Leu Phe Asp Tyr Ala Lys His Asp Leu Trp His Ile Ile Asn Phe His
                100                 105                 110 cgt gca tca aaa gca aat aaa aag ccc atg cag tta cca aaa tcc atg        443
Arg Ala Ser Lys Ala Asn Lys Lys Pro Met Gln Leu Pro Lys Ser Met
                115                 120                 125 gtt aaa tca ctg ctg tac cag atc ctc gat ggc atc cat tac ctc cac        491
Val Lys Ser Leu Leu Tyr Gln Ile Leu Asp Gly Ile His Tyr Leu His
            130                 135                 140 gca aac tgg gtg ctc cac agg gac ctg aaa cca gca aat atc cta gta        539
Ala Asn Trp Val Leu His Arg Asp Leu Lys Pro Ala Asn Ile Leu Val
145                 150                 155 atg gga gaa ggt cct gaa agg ggg aga gtc aaa ata gct gac atg ggt        587
Met Gly Glu Gly Pro Glu Arg Gly Arg Val Lys Ile Ala Asp Met Gly
160                 165                 170                 175 ttt gcc agg tta ttc aat tct ccc cta aag cca ctc gca gat ttg gat        635
Phe Ala Arg Leu Phe Asn Ser Pro Leu Lys Pro Leu Ala Asp Leu Asp
                180                 185                 190 cca gtg gtt gtg aca ttt tgg tat cgg gct ccg gaa ctt tta ctt ggt        683
Pro Val Val Val Thr Phe Trp Tyr Arg Ala Pro Glu Leu Leu Leu Gly
            195                 200                 205 gcc agg cat tac aca aag gcc att gac atc tgg gca ata ggc tgc ata        731
Ala Arg His Tyr Thr Lys Ala Ile Asp Ile Trp Ala Ile Gly Cys Ile
        210                 215                 220 ttt gct gaa ctc ttg act tca gaa ccc att ttt cac tgt cgt cag gag        779
Phe Ala Glu Leu Leu Thr Ser Glu Pro Ile Phe His Cys Arg Gln Glu
    225                 230                 235 gat ata aaa aca agc aat cct ttt cat cat gat cag tta gat cga ata        827
Asp Ile Lys Thr Ser Asn Pro Phe His His Asp Gln Leu Asp Arg Ile
240                 245                 250                 255 ttt agt gtc atg ggg ttt cct gca gat aaa gac tgg gaa gat att aga        875
Phe Ser Val Met Gly Phe Pro Ala Asp Lys Asp Trp Glu Asp Ile Arg
                260                 265                 270 aaa atg cca gag tac cca aca ctt cag aaa gac ttt cga aga aca acg        923
Lys Met Pro Glu Tyr Pro Thr Leu Gln Lys Asp Phe Arg Arg Thr Thr
            275                 280                 285 tac gcc aac agc agc ctc ata aaa tac atg gag aag cac aag gtc aag        971
Tyr Ala Asn Ser Ser Leu Ile Lys Tyr Met Glu Lys His Lys Val Lys
        290                 295                 300
```

-continued

| | | |
|---|---|---|
| cct gac agc aaa gtg ttc ctc ctg ctt cag aaa ctc ctc acc atg gat<br>Pro Asp Ser Lys Val Phe Leu Leu Leu Gln Lys Leu Leu Thr Met Asp<br>305                     310                    315 | 1019 |

```
cct gac agc aaa gtg ttc ctc ctg ctt cag aaa ctc ctc acc atg gat     1019
Pro Asp Ser Lys Val Phe Leu Leu Leu Gln Lys Leu Leu Thr Met Asp
305                 310                 315 cca acc aag aga atc acc tca gag cag gct ctg cag gac cct tac ttc     1067
Pro Thr Lys Arg Ile Thr Ser Glu Gln Ala Leu Gln Asp Pro Tyr Phe
320                 325                 330                 335 cag gaa gac ccc ctg cca aca tta gat gtg ttc gct ggc tgc cag att     1115
Gln Glu Asp Pro Leu Pro Thr Leu Asp Val Phe Ala Gly Cys Gln Ile
                340                 345                 350 ccg tac ccc aaa aga gaa ttc ctt aat gaa gat gaa cca gaa gag aaa     1163
Pro Tyr Pro Lys Arg Glu Phe Leu Asn Glu Asp Glu Pro Glu Glu Lys
            355                 360                 365 ggt gac aag aac cag cca cag cag cag aac cca cat cag caa cct gca     1211
Gly Asp Lys Asn Gln Pro Gln Gln Gln Asn Pro His Gln Gln Pro Ala
        370                 375                 380 gcc ccc gca cag cag aca gca gcc ccc cca cag gct cct cca cca cag     1259
Ala Pro Ala Gln Gln Thr Ala Ala Pro Pro Gln Ala Pro Pro Pro Gln
385                 390                 395 cag agc agt gcc caa acc aat gga act gct ggg gga gcc act gcg gga     1307
Gln Ser Ser Ala Gln Thr Asn Gly Thr Ala Gly Gly Ala Thr Ala Gly
400                 405                 410                 415 ggc ggg ggc gct gga gcg ggg ctg cag cac agc cag gac ccc ggg ctg     1355
Gly Gly Gly Ala Gly Ala Gly Leu Gln His Ser Gln Asp Pro Gly Leu
                420                 425                 430 aat cag gtg cct cca aac aag aag ccc cgg att ggg cct tcc ggt gca     1403
Asn Gln Val Pro Pro Asn Lys Lys Pro Arg Ile Gly Pro Ser Gly Ala
            435                 440                 445 aac tca ggc ggg ccc gtt atg ccg tcg gat tat cag cat tcc agt tct     1451
Asn Ser Gly Gly Pro Val Met Pro Ser Asp Tyr Gln His Ser Ser Ser
        450                 455                 460 cgc ctg aat tac caa agc agc gta cag ggg tcc tct cag tcc cag agt     1499
Arg Leu Asn Tyr Gln Ser Ser Val Gln Gly Ser Ser Gln Ser Gln Ser
465                 470                 475 acg cta ggc tac tct tca tct caa cag agt acc cag tac cac tca tct     1547
Thr Leu Gly Tyr Ser Ser Ser Gln Gln Ser Thr Gln Tyr His Ser Ser
480                 485                 490                 495 cac cag acc cac cgg tac tgacccactc cctctgcttg gccttggact            1595
His Gln Thr His Arg Tyr
                500 ccagcagggt ggtatttgtg ttacaaagac ccccagaatg aagactgaca ccatgcaaag   1655 tgcagaccct tgagaggaaa cctttgcatg taagtgtttt gaaggactaa gctctcttct   1715 tcattgacta aaagaggatt cttgtgaagt gtccccgccc tcttcccccg catgatttcc   1775 tctgtgactt tcctgatgaa gcctctgatc tacccagcac ttctgcatcc ttcagcagtc   1835 tctgagggaa tttctggtgc acctttctca cgctgtagca atcattataa tttatctttt   1895 cttagagttt caatgttgta ggcacagggt tccagtggtg tatagtttta tacttcatga   1955 actgatttag caacaccagt gaaatgcacc ttttaaagca ctccacagtc tccacagact   2015 aactgctctg ctcttggaag tcttcaaaag aaactgttac tgtcccaaag tactttacta   2075 ttatgttttt atttatctct ttcagggaag gtgaaagaca gtgtgggaca gacggtgccc   2135 acaaccaaaa acagtgtagg tctttgcagc tacctgctta tgctatgaaa aactgaagta   2195 cttggtgatt tttatataat cattcatggg gaactcagtt cccagaatca tcatattctg   2255 aataatattc agtaattaaa attataattt taacttcatg tagctaagtc tactttaaaa   2315 gaggtttcaa gagctttgac ggaatccagt cctttggac tcacctggga agtctgaaga    2375 gcctgtttcc tgcactagga cctcacaagg agtcacgctg atcaaagcac gcttcttcca   2435
```

```
cgtgaaggaa aagcttttcc catgtgtgtc ttcagacgct tctctcaagg ggctgctggc    2495
tcttcagtct cttcacatgg ggtcagcatg agtaacttc ttccataatc aaggatactc    2555
aaatagaagc ttgttcattc atctgcaggg ttttccattt gtgtgtacat taagcataaa    2615
gtgactattt ttaaagcatg ttaaaatttt aggtttcatt catgtttgaa gtgtgtatta    2675
tgtatgcata attttgctgt tactgagact taacgctgtc aagaatcttt tgtattgcac    2735
tgaatgcttt cttttgcccc taggacaaaa accttaataa ttgtgcctaa gaactatggg    2795
cagatagtgt aaagtagatg aggtgaatat ttgcatttcc atgatctacg aattagaggg    2855
gagttctatt ttagctactt ttgaggaacc cccacctcca gaatcaagag gaaatgtaaa    2915
ggcttagagc tcccagtgta gtgcaggggc agaacacctg tgttctgatg ctcctagcag    2975
caccagcctt gtttgcaatg tttcttgagc tagaaaaaaa tagccaattg tatatgcaaa    3035
ctatatgcat ttttaaaaaa ctattcttgt gaacctatct acctggttat gatactctgg    3095
ggtccatata caagtaaaat aagatttta gaagccagta tacattttgc actattgatg    3155
tgatactgta gccagccagg accacactga tttcagcata aggatgctta taaacagtaa    3215
taaaggctgt atggtggcat gcataccagg gccgaaaatg aagtcattga catgtgacat    3275
gcttcactgg gaggaatctc tgactgtctc cttagacttt ttttttaat cccttatatt    3335 tttttaaaat aagaatcagc cttgtgcata atgtcactat caatataaag ttctgtcctg    3395
tgccctggag cctctttgtc cagggccact gctcccttct cacaggctca gtgctctgct    3455
gggaagaaaa cataaagagt gggagacatt tccttattgc agccagtcca gtgatcataa    3515
gctcctgtgg gctgtgcgcg ccctgtgact gacttataaa tgccctgtga gatgaaggtc    3575
ctttgtttac ttctcaaccc acttggataa gtatgcttcc gacttttatg gtaaacagtg    3635
ttatggggaa gcaggtctgt gtctgagcac ttgaggagaa agccagtgat tagctgtcac    3695
aaaaggcatc tatgcatatt tgaaatgttc acagcagcct tcagcagcag ttgggtggcc    3755
cttgtggaca gagcatattc tactaagtgg ttgtagagaa ttacaatgaa aatagaagct    3815
ctgttcttgc cctcgaatga gctcaattta ataaagaca ttagcccta aaaaaaaaa    3875 aaaaaaaaaa aaaaaa                                                   3891
```

<210> SEQ ID NO 4
<211> LENGTH: 501
<212> TYPE: PRT
<213> ORGANISM: mouse

<400> SEQUENCE: 4

```
Met Asp Tyr Asp Phe Lys Ala Lys Leu Ala Ala Glu Arg Glu Arg Val
  1               5                  10                  15

Glu Asp Leu Phe Glu Tyr Glu Gly Cys Lys Val Gly Arg Gly Thr Tyr
                 20                  25                  30

Gly His Val Tyr Lys Ala Arg Arg Lys Asp Gly Lys Asp Glu Lys Glu
             35                  40                  45

Tyr Ala Leu Lys Gln Ile Glu Gly Thr Gly Ile Ser Met Ser Ala Cys
         50                  55                  60

Lys Glu Ile Ala Leu Leu Arg Glu Leu Asn His Pro Asn Val Ile Ala
 65                  70                  75                  80

Leu Gln Lys Val Phe Leu Ser His Ser Asp Arg Lys Val Trp Leu Leu
                 85                  90                  95

Phe Asp Tyr Ala Lys His Asp Leu Trp His Ile Ile Asn Phe His Arg
                100                 105                 110
```

-continued

```
Ala Ser Lys Ala Asn Lys Lys Pro Met Gln Leu Pro Lys Ser Met Val
        115                 120                 125

Lys Ser Leu Leu Tyr Gln Ile Leu Asp Gly Ile His Tyr Leu His Ala
130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
            180                 185                 190

Val Val Val Thr Phe Trp Tyr Arg Ala Pro Glu Leu Leu Leu Gly Ala
        195                 200                 205

Arg His Tyr Thr Lys Ala Ile Asp Ile Trp Ala Ile Gly Cys Ile Phe
    210                 215                 220

Ala Glu Leu Leu Thr Ser Glu Pro Ile Phe His Cys Arg Gln Glu Asp
225                 230                 235                 240

Ile Lys Thr Ser Asn Pro Phe His His Asp Gln Leu Asp Arg Ile Phe
                245                 250                 255

Ser Val Met Gly Phe Pro Ala Asp Lys Asp Trp Glu Asp Ile Arg Lys
            260                 265                 270

Met Pro Glu Tyr Pro Thr Leu Gln Lys Asp Phe Arg Arg Thr Thr Tyr
        275                 280                 285

Ala Asn Ser Ser Leu Ile Lys Tyr Met Glu Lys His Lys Val Lys Pro
    290                 295                 300

Asp Ser Lys Val Phe Leu Leu Gln Lys Leu Leu Thr Met Asp Pro
305                 310                 315                 320

Thr Lys Arg Ile Thr Ser Glu Gln Ala Leu Gln Asp Pro Tyr Phe Gln
                325                 330                 335

Glu Asp Pro Leu Pro Thr Leu Asp Val Phe Ala Gly Cys Gln Ile Pro
            340                 345                 350

Tyr Pro Lys Arg Glu Phe Leu Asn Glu Asp Glu Pro Glu Glu Lys Gly
        355                 360                 365

Asp Lys Asn Gln Pro Gln Gln Asn Pro His Gln Gln Pro Ala Ala
    370                 375                 380

Pro Ala Gln Gln Thr Ala Ala Pro Pro Gln Ala Pro Pro Gln Gln
385                 390                 395                 400

Ser Ser Ala Gln Thr Asn Gly Thr Ala Gly Ala Thr Ala Gly Gly
                405                 410                 415

Gly Gly Ala Gly Ala Gly Leu Gln His Ser Gln Asp Pro Gly Leu Asn
            420                 425                 430

Gln Val Pro Pro Asn Lys Lys Pro Arg Ile Gly Pro Ser Gly Ala Asn
        435                 440                 445

Ser Gly Gly Pro Val Met Pro Ser Asp Tyr Gln His Ser Ser Ser Arg
    450                 455                 460

Leu Asn Tyr Gln Ser Ser Val Gln Gly Ser Ser Gln Ser Gln Ser Thr
465                 470                 475                 480

Leu Gly Tyr Ser Ser Ser Gln Ser Thr Gln Tyr His Ser Ser His
                485                 490                 495

Gln Thr His Arg Tyr
            500

<210> SEQ ID NO 5
<211> LENGTH: 464
<212> TYPE: PRT
<213> ORGANISM: human
```

```
<400> SEQUENCE: 5

Met Asp Tyr Asp Phe Lys Val Lys Leu Ser Ser Arg Glu Arg Val
 1               5                  10                  15

Glu Asp Leu Phe Glu Tyr Glu Gly Cys Lys Val Gly Arg Gly Thr Tyr
             20                  25                  30

Gly His Val Tyr Lys Ala Lys Arg Lys Asp Gly Lys Asp Asp Lys Asp
             35                  40                  45

Tyr Ala Leu Lys Gln Ile Glu Gly Thr Gly Ile Ser Met Ser Ala Cys
     50                  55                  60

Arg Glu Ile Ala Leu Leu Arg Glu Leu Lys His Pro Asn Val Ile Ser
 65                  70                  75                  80

Leu Gln Lys Val Phe Leu Ser His Ala Asp Arg Lys Val Trp Leu Leu
                 85                  90                  95

Phe Asp Tyr Ala Glu His Asp Leu Trp His Ile Ile Lys Phe His Arg
                100                 105                 110

Ala Ser Lys Ala Asn Lys Lys Pro Val Gln Leu Pro Arg Gly Met Val
                115                 120                 125

Lys Ser Leu Leu Tyr Gln Ile Leu Asp Gly Ile His Tyr Leu His Ala
    130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
                180                 185                 190

Val Val Val Thr Phe Trp Tyr Arg Ala Pro Glu Leu Leu Leu Gly Ala
            195                 200                 205

Arg His Tyr Thr Lys Ala Ile Asp Ile Trp Ala Ile Gly Cys Ile Phe
    210                 215                 220

Ala Glu Leu Leu Thr Ser Glu Pro Ile Phe His Cys Arg Gln Glu Asp
225                 230                 235                 240

Ile Lys Thr Ser Asn Pro Tyr His His Asp Gln Leu Asp Arg Ile Phe
                245                 250                 255

Asn Val Met Gly Phe Pro Ala Asp Lys Asp Trp Glu Asp Ile Lys Lys
            260                 265                 270

Met Pro Glu His Ser Thr Leu Met Lys Asp Phe Arg Arg Asn Thr Tyr
    275                 280                 285

Thr Asn Cys Ser Leu Ile Lys Tyr Met Glu Lys His Lys Val Lys Pro
290                 295                 300

Asp Ser Lys Ala Phe His Leu Leu Gln Lys Leu Leu Thr Met Asp Pro
305                 310                 315                 320

Ile Lys Arg Ile Thr Ser Glu Gln Ala Met Gln Asp Pro Tyr Phe Leu
                325                 330                 335

Glu Asp Pro Leu Pro Thr Ser Asp Val Phe Ala Gly Cys Gln Ile Pro
            340                 345                 350

Tyr Pro Lys Arg Glu Phe Leu Thr Glu Glu Pro Asp Asp Lys Gly
    355                 360                 365

Asp Lys Lys Asn Gln Gln Gln Gln Gly Asn Asn His Thr Asn Gly
370                 375                 380

Thr Gly His Pro Gly Asn Gln Asp Ser Ser His Thr Gln Gly Pro Pro
385                 390                 395                 400

Leu Lys Lys Val Arg Val Val Pro Thr Thr Thr Ser Gly Gly Leu
                405                 410                 415
```

-continued

```
Ile Met Thr Ser Asp Tyr Gln Arg Ser Asn Pro His Ala Ala Tyr Pro
            420                 425                 430

Asn Pro Gly Pro Ser Thr Ser Gln Pro Gln Ser Ser Met Gly Tyr Ser
            435                 440                 445

Ala Thr Ser Gln Gln Pro Pro Gln Tyr Ser His Gln Thr His Arg Tyr
            450                 455                 460

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:peptide
                        motif

<400> SEQUENCE: 6

Ser Ala Cys Arg Glu
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:cyclin-
                        binding domain

<400> SEQUENCE: 7

Pro Ser Thr Ala Ile Glu
 1               5
```